United States Patent [19]

Fujimiya et al.

[11] Patent Number: 5,706,498

[45] Date of Patent: Jan. 6, 1998

[54] GENE DATABASE RETRIEVAL SYSTEM WHERE A KEY SEQUENCE IS COMPARED TO DATABASE SEQUENCES BY A DYNAMIC PROGRAMMING DEVICE

[75] Inventors: Hitoshi Fujimiya, Mobara; Shinichiro Yamamoto, Chiba; Norio Maru, Mobara; Toshitsugu Okayama; Hisanori Nasu, both of Yokohama, all of Japan

[73] Assignees: Hitachi Device Engineering Co., Ltd., Chiba-ken; Hitachi Software Engineering Co., Ltd., Kanagawa-ken, both of Japan

[21] Appl. No.: 312,689

[22] Filed: Sep. 26, 1994

[30] Foreign Application Priority Data

Sep. 27, 1993 [JP] Japan ............................ 5-260403

[51] Int. Cl.⁶ .......................... G06F 17/30; G06F 13/12
[52] U.S. Cl. ...................... 395/606; 364/413.1; 364/497; 435/6; 935/77; 395/800
[58] Field of Search ....................... 395/600, 606, 395/800; 364/413.01, 413.1, 728.03, 728.05, 728.07; 435/6; 935/80, 77, 87

[56] References Cited

U.S. PATENT DOCUMENTS

| | | | |
|---|---|---|---|
| 4,939,666 | 7/1990 | Hardman | 364/496 |
| 5,526,463 | 6/1996 | Gillick et al. | 395/26 |
| 5,534,438 | 7/1996 | Haydon et al. | 435/320.1 |
| 5,577,249 | 11/1996 | Califano | 395/611 |
| 5,595,877 | 1/1997 | Gold et al. | 435/6 |

OTHER PUBLICATIONS

A.F.W. Coulson et al, "Protein and Nucleic Acid Sequence Database Searching: A Suitable Case for Parallel Processing", The Computer Journal, vol. 30, No. 5, 1987, pp. 420–424.

D.T. Hoang, "Searching Genetic Databases on Splash 2", FPGAs For Custom Computing Machines, Apr. 5–7, 1993, pp. 185–191.

E. Lander, "Protein Sequence Comparison on a Data Parallel Computer", 1988 International Conference On Parallel Processing, Aug. 15–19, 1988, pp. 257–263.

T. Barsalou, M.D. et al, "Searching Gene and Protein Sequence Databases", M.D. Computing, vol. 8, No. 3, 1991, pp. 144–149.

Megson, G. M., "Efficient Systolic String Matching", Electronic Letters, vol. 26, No. 24, pp. 2040–2042, Nov. 1990.

Cohen, R., "Resurchers Inherit DNA–analysis Database", MacWEEK, vol. 6, No. 11, p. 8, Mar. 1992.

Bunke, H., "Edit Distanceof Run–Lenght Coded Strings", Applied Computing: Technological Challenges of the 1990's vol. 1, pp. 137–143, Mar. 1992.

Khan, A. S., "Single pass sequencingand the physical and genetic mapping of human brain cDNAs", nature genetics, vol. 2, pp. 180–185, Nov. 1992.

Arnold J. M. et al., "The Splash 2 Processor and Applications", Computer Design ICCD '93, pp. 482–485, Oct. 1993.

*Primary Examiner*—Thomas G. Black
*Assistant Examiner*—Jack M. Choules
*Attorney, Agent, or Firm*—Fay, Sharpe, Beall, Fagan, Minnich & McKee

[57] ABSTRACT

The gene database retrieval system, for making a retrieval for a gene sequence having a sequence similar to a sequence data from a gene database, contains a gene database for storing the sequence data of genes whose structures or sequences have already been analyzed and identified, a dynamic programming operation unit for determining the degree of similarity between target data and key data by utilizing the sequence data of the bases of the gene from the gene database as the target data and the sequence data of the bases as the key for retrieval, and a central processing device unit for executing the access process to make access to the gene database, in parallel to the operation process for determining the degree of similarity by transmitting the sequence data of the bases from the gene database continually one after another into the dynamic programming operation unit as the target data, by controlling the gene database and the dynamic programming operation unit.

12 Claims, 10 Drawing Sheets

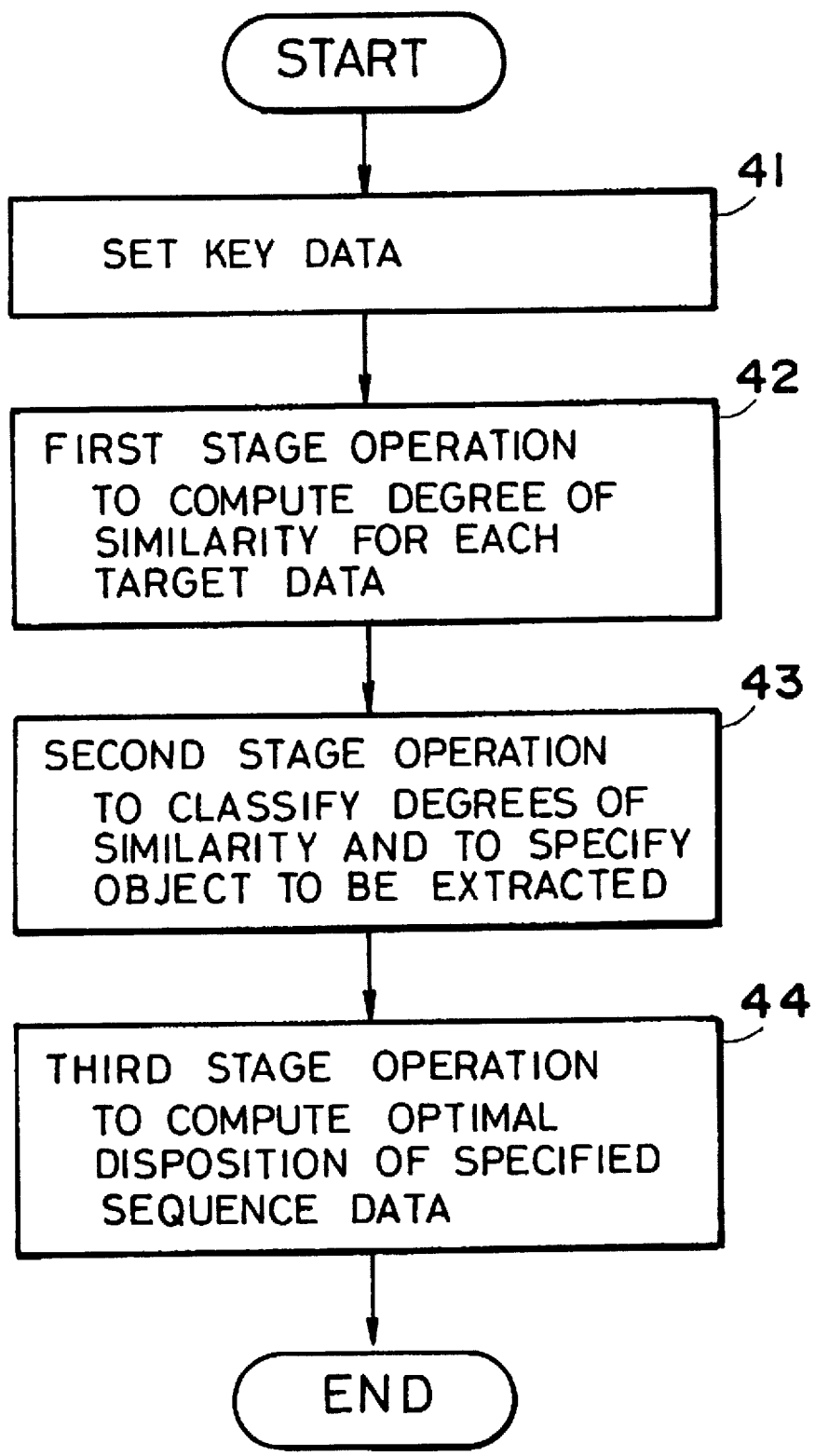

FIG. 5a

|   | A | C | G | T | R | Y | M | W | S | K | D | H | V | B | N |
|---|---|---|---|---|---|---|---|---|---|---|---|---|---|---|---|
| A | 4 | -2 | -2 | -2 | 2 | -1 | 2 | 2 | -1 | -1 | 2 | 2 | 2 | -1 | 2 |
| C | -2 | 4 | -2 | -2 | -1 | 2 | 2 | -1 | 2 | -1 | -1 | 2 | 2 | 2 | 2 |
| G | -2 | -2 | 4 | -2 | 2 | -1 | -1 | -1 | 2 | 2 | 2 | -1 | 2 | 2 | 2 |
| T | -2 | -2 | -2 | 4 | -1 | 2 | -1 | 2 | -1 | 2 | 2 | 2 | -1 | 2 | 2 |
| R | 2 | -1 | 2 | -1 | 2 | -2 | 0 | 0 | 0 | 2 | 0 | 2 | 0 | 0 | 0 |
| Y | -1 | 2 | -1 | 2 | -2 | 2 | 0 | 0 | 0 | 0 | 2 | 0 | 2 | 0 | 0 |
| M | 2 | 2 | -1 | -1 | 0 | 0 | 2 | 0 | 0 | 0 | 0 | 2 | 2 | 0 | 0 |
| W | 2 | -1 | -1 | 2 | 0 | 0 | 0 | 2 | 0 | 0 | 2 | 2 | 0 | 0 | 0 |
| S | -1 | 2 | 2 | -1 | 0 | 0 | 0 | 0 | 2 | 0 | 0 | 0 | 2 | 2 | 0 |
| K | -1 | -1 | 2 | 2 | 0 | 0 | 0 | 0 | 0 | 2 | 2 | 0 | 0 | 2 | 0 |
| D | 2 | -1 | 2 | 2 | 2 | 0 | 0 | 2 | 0 | 2 | 2 | 0 | 0 | 0 | 0 |
| H | 2 | 2 | -1 | 2 | 0 | 2 | 2 | 2 | 0 | 0 | 0 | 2 | 0 | 0 | 0 |
| V | 2 | 2 | 2 | -1 | 2 | 0 | 2 | 0 | 2 | 0 | 0 | 0 | 2 | 0 | 0 |
| B | -1 | 2 | 2 | 2 | 0 | 2 | 0 | 0 | 2 | 2 | 0 | 0 | 0 | 2 | 0 |
| N | 0 | 0 | 0 | 0 | 0 | 0 | 0 | 0 | 0 | 0 | 0 | 0 | 0 | 0 | 0 |

TARGET-SIDE DATA →

KEY-SIDE DATA →

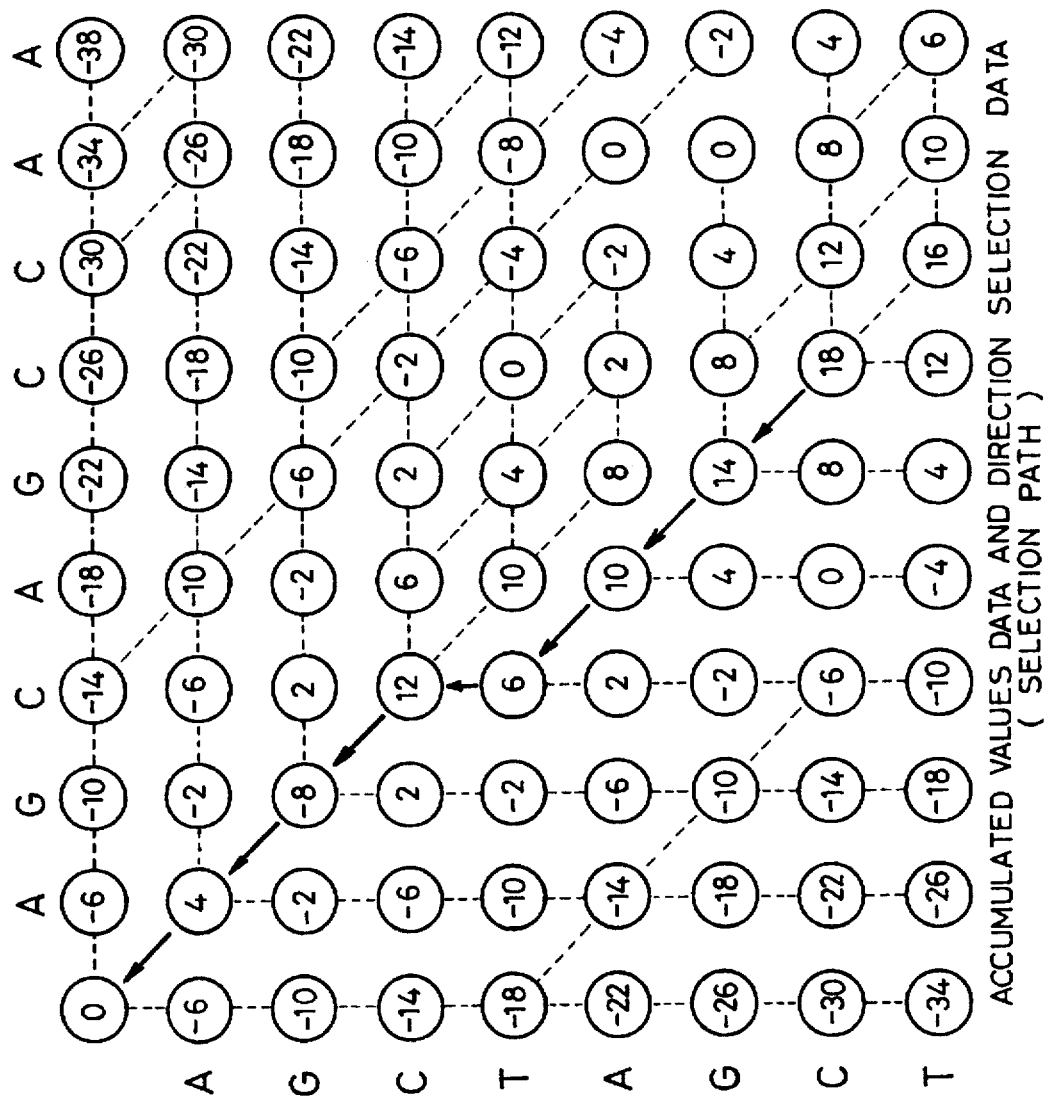

TARGET-SIDE DATA →     81

| | A | C | G | T | R | Y | M | W | S | K | D | H | V | B | N |
|---|---|---|---|---|---|---|---|---|---|---|---|---|---|---|---|
| A | 4 | -2 | -2 | -2 | 2 | -1 | 2 | 2 | -1 | -1 | 2 | 2 | 2 | -1 | 2 |
| C | -2 | 4 | -2 | -2 | -1 | 2 | 2 | -1 | 2 | -1 | -1 | 2 | 2 | 2 | 2 |
| G | -2 | -2 | 4 | -2 | 2 | -1 | -1 | -1 | 2 | 2 | 2 | -1 | 2 | 2 | 2 |
| T | -2 | -2 | -2 | 4 | -1 | 2 | -1 | 2 | -1 | 2 | 2 | 2 | -1 | 2 | 2 |
| R | 2 | -1 | 2 | -1 | 2 | -2 | 0 | 0 | 0 | 0 | 2 | 0 | 2 | 0 | 0 |
| Y | -1 | 2 | -1 | 2 | -2 | 2 | 0 | 0 | 0 | 0 | 0 | 2 | 0 | 2 | 0 |
| M | 2 | 2 | -1 | -1 | 0 | 0 | 2 | 0 | 0 | 0 | 0 | 2 | 2 | 0 | 0 |
| W | 2 | -1 | -1 | 2 | 0 | 0 | 0 | 2 | 0 | 0 | 2 | 2 | 0 | 0 | 0 |
| S | -1 | 2 | 2 | -1 | 0 | 0 | 0 | 0 | 2 | 0 | 0 | 0 | 2 | 2 | 0 |
| K | -1 | -1 | 2 | 2 | 0 | 0 | 0 | 0 | 0 | 2 | 2 | 0 | 0 | 2 | 0 |
| D | 2 | -1 | 2 | 2 | 2 | 0 | 0 | 2 | 0 | 2 | 2 | 0 | 0 | 0 | 0 |
| H | 2 | 2 | -1 | 2 | 0 | 2 | 2 | 2 | 0 | 0 | 0 | 2 | 0 | 0 | 0 |
| V | 2 | 2 | 2 | -1 | 2 | 0 | 2 | 0 | 2 | 0 | 0 | 0 | 2 | 0 | 0 |
| B | -1 | 2 | 2 | 2 | 0 | 2 | 0 | 0 | 2 | 2 | 0 | 0 | 0 | 2 | 0 |
| N | 2 | 2 | 2 | 2 | 0 | 0 | 0 | 0 | 0 | 0 | 0 | 0 | 0 | 0 | 2 |

KEY-SIDE DATA ↓

( SYMBOLS "A" TO "N" REFER TO BASES CODES. )

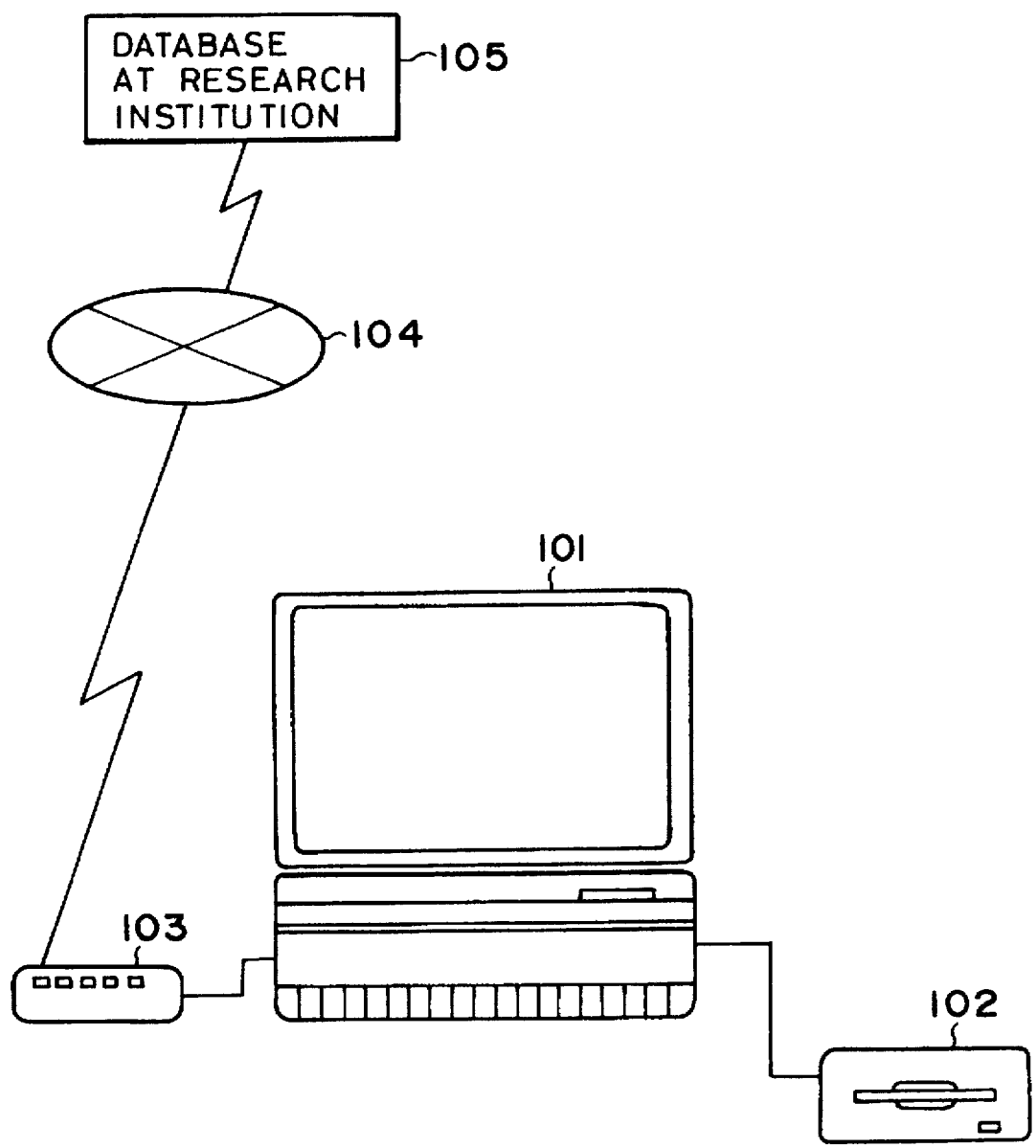

GENE DATABASE RETRIEVAL SYSTEM WHERE A KEY SEQUENCE IS COMPARED TO DATABASE SEQUENCES BY A DYNAMIC PROGRAMMING DEVICE

BACKGROUND OF INVENTION

1. Field of the Invention

The present invention relates to a gene database retrieval system and, more particularly, to a gene database retrieval system so adapted as to effectively execute an operation of the retrieval for a gene sequence, and to make retrieval for a sequence data of the gene sequence from a gene database having sequence data of sequences of bases of nucleic acids and/or sequences of amino acids of genes whose structures have already been analyzed, when the retrieval for the gene sequence is made using a gene sequence similar thereto as a candidate for extracting a sequence data of the gene sequence from the gene database.

2. Description of the Related Art

There has currently been made active research and development work for the purpose of analyzing characteristics of animal and plant species at gene levels, such as human genome projects and rice plant genome projects. Such research and development activities are based on the understanding that expression and generation of functions, useful for the human being, in and from another biological body can be realized by the established gene recombinant technology and that each of the characteristics of such an organism can correspond to a sequence at gene levels.

Hitherto, the structures of gene sequences of some organisms have been analyzed, and information of the resultant gene sequences has already been registered in databases for common use. General researchers can make access to such databases and utilize the information of the gene sequences registered therein. Such databases include, for example, GenBank in the U.S., EMBL in Europe, Gene Database at National Gene Institute of Japan, and so on.

In the description of this specification, the term "gene" is intended to mean a sequence of bases of a nucleic acid having information of a gene of an organism or a sequence of bases of amino acids in combination with the sequence of the bases of such a nucleic acid, unless otherwise stated herein.

The retrieval for gene sequences from the gene database is performed to assume the functions in the living body of the gene sequences determined experimentally by researchers; to form a genetic cladogram by grouping the living bodies having homologous sequences; or to determine whether the structure and the genetic information of the gene sequence determined experimentally by the researcher have already been discovered.

A description will now be made of an example of operations for the retrieval of a gene sequence from a gene database hitherto accessible. In order to analyze and determine the function inherent only in a particular organism, many researchers are searching for a mechanism that controls and governs the function of the organism. In many occasions, a protein or its peripheral saccharide intermediates or intermediate constitute such a mechanism.

The sequence of bases of the nucleic acid having the gene information can then be determined from the high molecular compound involved in the clarified mechanism. For example, for a protein, the sequence of the amino acid residues is determined and the sequence of the amino acids is then allowed to correspond to a codon of a gene. It cannot be said in some cases, however, that the assumed gene sequence is thoroughly analyzed and determined because some modifications may be caused to appear, when the sequence of the bases of the nucleic acid is to be translated into a protein, and plural codons may correspond to one amino acid residue.

The retrieval for the gene database can be made, however, on the basis of the assumed gene sequence, thereby enabling the organism function having the homologous gene sequence to be retrieved. From the results of the retrieval for the organism functions from the gene database, a gene probe can be prepared on the basis of the gene sequence having a high degree of retrieval accuracy. By binding the gene probe to a chromosome of the objective organism, it is possible to analyze and determine the position of the chromosome in which the involved gene information is located.

In addition, it is further possible to analyze and determine the final sequence of the bases by extracting the portion of the gene probe bound to the chromosome. In some cases, the gene database is retrieved directly by the sequence of the amino acids. As described hereinabove, the retrieval for the sequence data of the sequences of the bases of the nucleic acid or the sequences of the amino acids from the gene database is essential for analyzing the mechanism of the organism.

The gene database retrieval of this kind is different from the retrieval for the database in a usual sense, in that a sequence having a high degree of similarity with respect to a sequence data serving as a key for retrieval is extracted from the gene database as a candidate for the result of retrieval. The retrieval for the gene database in such a fashion is referred to as a homology retrieval.

It is to be noted herein that, for biologically high-molecular compounds such as genes, the gene sequences may vary gradually with generation and that, as plural generations pass, deficiency or insertion of a gene piece or pieces may be caused to occur from or into the sequence or sequences of the gene involved. In order that similarity between the gene sequences having such properties is assessed with the insertion or deficiency of the portion of the gene sequence in its optional position taken into account, a solution to the direct assessment requires to carry out the computation of an enormously great volume of information to give a result of assessment. In order to reduce such an enormous volume of computation, a technique of approximate computation according to a solution to dynamic programming is employed in usual cases.

The typical solution to the assessment for determining similarity between the gene sequences is constituted by steps as will be described hereinafter, in order to reduce the amount of enormous combinations of data and to proceed with operations with high efficiency by utilizing the technique for the solution to dynamic programming for determining an optimal solution as a whole. The typical technique comprises the step of determining if a minute portion of an object, e.g. one base of a gene, agrees with the corresponding portion of an identified object; the step of summing up points from the starting point of the operation by adding together increments when it is decided that the portions (bases) thereof agree with each other and by subtracting decrements when it is decided that the insertion or deficiency of such a minute portion occurs into or from the gene sequence; the step of determining a locally optimal path for each of the combinations of data from the first combination to the last combination; and the step of determining an optimal combination as a whole by tracing the locally selected paths determined in the previous step in the backward or opposite direction ("back-tracing") from the point at which the largest sum is obtained.

Then, a description will be made of a specific example in which the retrieval for data from a gene database is executed by means of the technique for the solution to the dynamic programming. FIGS. 7a and 7b are diagrams indicating the principle of the operation method for computing the degree of similarity between the gene sequences on the basis of the technique by the dynamic programming. FIG. 7a indicates the wholly operating flow of the dynamic programming, and FIG. 7b indicates a diagram for a description of the operation principle of operating basic operation cells or squares for the dynamic programming.

As shown in FIG. 7a, for example, a sequence data of bases (a key data) functioning as a retrieval key and a sequence data of bases (a target data) extracted from a gene database are arranged on the column and the row, i.e. on the y-axial side and on the x-axial side extending at the right angle to the y-axial side, respectively, in such a manner that the combinations of the key data on the y-axial side with the target data on the x-axial side form squares or cells which in turn are arranged in the form of a matrix. Then, each of the element data of the key data on the y-axial side is compared with each of the element data of the target data on the x-axial side in each of the squares or cells of the matrix, in order to make a decision to determine if both of the element data between the key data and the target data are equal to or agreeable with each other or if the difference in the two element data therebetween would be considered to occur merely due to substitution. When it is decided that the element data of the key data is equal to or agreeable with that of the target data or that the difference between the element data therebetween is caused to occur merely due to substitution, the solid and oblique arrow (path) is drawn diagonally in the corresponding square or cell and the involved point of the square or cell is provided with a higher score in order to give a higher score to the path selected.

On the other hand, if it is assumed due to the insertion or deficiency of an element of the sequence data (or the key data) into or from another sequence data (or the target data) that the sequence data as the target data constituting a pair with the key data does not exist in the square or cell of the matrix, that is, that the element of the one sequence data differs from the element of the other sequence data, the bar extending at a right angle between the two element data is regarded as a path and a decrement is subtracted from the score value at this point of the path. With this arrangement of the paths as indicated by the combinations of the oblique lines with the bars extending at right angles in the matrix, an optimal combination between the two elements can be represented. Further, the most agreeable combination of the target data with the key data, i.e. in which the target data agrees most with the key data (hereinafter referred to as "optimal disposition"), can be determined on the basis of the sum of the score values of the paths passing through the most agreeable combinations. Hence, the optimal path can be determined by computing the score value at each of the lattice points of the matrix and then determining the path by singling out the highest scored lattice point from each of the rows of the matrix and connecting the highest scored lattice points with each other. Accordingly, the determination of the optimal disposition can be said to be a question of determining the optimal path.

In order to compare the solution to this problem between when the dynamic programming is utilized and when no dynamic programming is utilized, a description will be made of an outline of the amount of computation when no dynamic programming is utilized and the optimal path is determined directly. In this case, the amount of computation is required so as to correspond to the number of the combinations of all paths, and it can be represented as S in Formula I, as will be indicated below, where reference symbol "M" denotes the number of elements of the first sequence data and reference symbol "N" denotes the number of elements of the second sequence data.

$$S = \sum_{r=0}^{\min(M,N)} \frac{(M+N-r)!}{(M-r)!(N-r)!r!}$$

For example, even if each of the numbers of the elements of the first and second sequence data is set to 10, i.e. M=N=10, in the above Formula I, the number S indicating the total number of combinations becomes as large as eight million. As is apparent from the foregoing, it is found that even if the number of the elements of the sequence data would be increased to a slight extent, the total number of computations becomes increased to an explosive extent. To the contrary, the process for the computation of the degree of similarity in the retrieval for the gene database by means of the dynamic programming can be performed by decreasing the number of computations to the order of the multiplication M×N (for example, in this case, to the order of 100 as M=N=10) by setting a variety of practical conditions.

Next, a description is made of the method for computation based on the dynamic programming. A similarity degree D(A, B) between a sequence A=a1, a2, ..., am and a sequence B=b1, b2, ..., bn is determined a posteriori. Further, the optimal disposition between a partial sequence As=a1, a2, ..., ai and a partial sequence Bs=b1, b2, ..., bj can be determined by utilizing one of three methods of disposition in the manner as described hereinafter.

First Method of Disposition:

After having the partial sequence As=a1, a2, ..., ai and the partial sequence Bs=b1, b2, ..., bs disposed in an optimal arrangement, a blank corresponding to "k" pieces of ingredients is inserted after the ingredient bj, and then the resultant sequence and a sequence a(i−k+1), ..., ai are caused to stand each other.

Second Method of Disposition:

After subjecting the partial sequence As=a1, a2, ..., a(i−1) and the partial sequence Bs=b1, b2, ..., b(j−1) to the optimal disposition, the ingredient bi and the ingredient bj are caused to stand each other.

Third Method of Disposition:

After having the partial sequence As=a1, a2, ..., ai and the partial sequence Bs=b1, b2, ..., b(j−k) disposed in an optimal arrangement, a blank corresponding to "k" pieces of ingredients is inserted after the ingredient bi, and then the resultant sequence and a sequence b(j−k+1), ..., bj are caused to stand each other.

Therefore, a similarity degree (a sum value), D(ai, bj), between the partial sequence As=a1, a2, ..., ai of the sequence A and the partial sequence Bs=b1, b2, ..., b(j−k) of the sequence B can be determined by solving a recurrence formula, as will be described hereinafter, when the similarity degree D(0, 0) by the score value at the initial condition is set to zero, i.e. D(0, 0)=0, given the condition in which the maximal length "α" of the sequence of the bases is inserted or lost at the one time. In the description which follows, as no confusion is made between the two sequences as the objects for determining the degree of similarity of one sequence with respect to the other when they do not vary, the similarity degree D(ai, bJ) is referred to simply as D(i, j). This expression is also intended to indicate a position (a matrix) of each element of an operation matrix of the sum values.

A large numeric value of the degree of similarity is termed, "resembling". In the expression of the following recurrence formula, the function 'min' of the operation of the dynamic programming is replaced with the function 'max'.

$$D(0, 0) = 0$$

When $1 \leq k \leq \alpha$, $$D(i, j) = \max[\max\{D(i-k, j) = v(k)\},$$
$$D(i-1, j-1) + \delta(ai, bj),$$
$$\max\{D(i, j-k) + v(k)\}]$$

where $0 \leq i \leq M$ and $0 \leq j \leq N$.

The parameters for solving this recurrence formula include "α", an insertion or deficiency score value, v(k), and a substitution score value, δ(ai, bj).

In order to further decrease the amount of computation, the parameter "α" is restricted to one. In other words, as no problem may occur from the practical point of view even if it is considered that insertion or deficiency occurs once or instantaneously by one piece only, k becomes one, i.e. k=1, by setting the parameter "α" to "1", i.e. α=1, so that the degree of similarity can be computed by the recurrence formula which follows:

$$D(0, 0) = 0$$
$$D(i, j) = \max[\max\{D(i-k, j) = v(k)\},$$
$$D(i-1, j-1) + \delta(ai, bj),$$
$$\max\{D(i, j-k) + v(k)\}]$$

where $0 \leq i \leq M$ and $0 \leq j \leq N$.

This operation can be typically expressed as indicated in FIG. 7b. Specifically, the operation of D(i, j) functions as a basic operation for selecting a path that can assume the maximal score value (sum value) among the three routes and for making a score for the corresponding lattice point (node) of the matrix. FIG. 7b indicates the contents of a cell or square for the basic operation for one lattice point (node) as shown in FIG. 7a. More specifically, in the basic operation cell or square as shown in FIG. 7b, the path (latitudinal lattice bar) as indicated by the arrow directed from above to down and the path (transverse lattice bar) as indicated by the arrow directed from left to right are intended to mean insertion or deficiency of a piece into or from the sequence data, while the path (oblique line) as indicated by the arrow directed diagonally in the cell or square is intended to mean substitution of a piece of the sequence data for another piece or coincidence of two sequence data.

Then, a description will be made of the actual procedures of computation. First, the score value (it may be positive or negative) of each route is added to each of the similarity degrees D(i-1, j), D(i-1, j-1) and D(i, j-1) at the three lattice points (nodes) of one cell or square of the matrix. Then, the largest value is selected from the resultant additions obtained from the three routes and the maximal value is set as a score of the node (lattice point) D(i, j) of the matrix of the sum values. This method is first applied to the origin (upper left corner point of the matrix) and then continued to be applied one after another to the lattice points (nodes) in the row direction or in the column direction, thereby making such a computation of the score of each of the nodes of the whole matrix and then finishing the basic operation.

Further, the wholly optimal disposition is determined, after the basic operations have been made in the manner as described hereinabove, by tracing the paths (the paths indicated by the lattice bars of the basic operation cells or the oblique lines thereof), selected upon the basic operation of each node (lattice point), in the backward or opposite direction ("back-tracing") from the last point or node located at the far right lower corner of the matrix, as indicated by reference numeral 71, in the upper left direction toward the lattice point or node of the matrix, i.e. the origin located at the far right upper corner of the matrix, thereby determining the whole path 71 at which the sum value of the scores at each of the rows or columns of the matrix values becomes maximal. Furthermore, likewise, a partially optimal disposition can be determined by back-tracing the selected paths in substantially the same way as described hereinabove from the lattice point or node that assumes the largest score value of the similarity degree D(i, j) determined at each of the lattice points or nodes.

The operation of the values of the matrix of the sum values representing the degrees of similarity can be made by computing the score value of the similarity degree D(i, j) at each lattice point or node one after another. The amount of computation in this case amounts to the (M×N)-fold order of the number of the steps of the basic operations. FIG. 8 indicates an example of symbols of gene sequence data to be actually available and its score table representing a score value of the score δ(ai, bj) when the base codes of a gene segment agree with each other or one base code of the gene segment is replaced with another base code.

In other words, FIG. 8 shows an example indicating a score table for determining degrees of similarity when the retrieval for a gene database is made using the dynamic programming. The score table 81 as shown in FIG. 8 is constituted by a table of a two-dimensional matrix type, for example, in which a data of the target-side sequence element data (ACGTRYMWSKDHVBN) is disposed in the row direction on the x-axial side of the matrix and a data of the key-side sequence element data (ACGTRYMWSKDHVBN) is disposed in the column direction on the y-axial side thereof. Each of the elements as referred to by the symbols (ACGTRYMWSKDHVBN) on the target side and on the key side indicates a base code, and the values of the score table indicate the score points to be added when the base codes agree with each other or when one base code is replaced with another.

By utilizing the technique for the solution to the dynamic programming in the manner as described hereinabove, the amount of computation required for assessment can be decreased to the order of multiplication M×N of the basic operations. This technique, however, requires a considerably long period of time for obtaining the result of assessment of the degrees of similarity in making the actual retrieval for a gene database.

In particular, it can be noted that it is difficult to improve a processing speed in the operation of the dynamic programming in this case, even if a usual-type processor for numeric operation would be utilized, because the operations for comparison should be made from three directions of each route in order to make selections of the paths, in addition to the operations for addition or subtraction of the score values, in the manner as described hereinabove. For example, when a gene data of about seventy thousand entries registered at the GenBank is retrieved for one key data, the retrieval time ranging from about ten and several hours to twenty hours is required even if an engineering workstation having the processing capacity corresponding to a data processing speed of about several ten MIPS would be utilized. Accordingly, there have been reviewed a variety of simplified techniques for shortening the operation time.

One example of the simplified techniques proposed with the attempt to further shorten the retrieval time involves, for example, determining a portion where sequences of characters agree with each other merely by disregarding the insertion or deficiency of a gene piece and failing to make a direct application of the dynamic programming, selecting a candidate by providing the length of the sequence portion of agreement with points, and applying the dynamic programming locally to only the agreed sequence portion as the object.

From the background that neither insertion nor deficiency of the base element or elements in the gene sequence are taken into account in the operations at its initial stage in the manner as described hereinabove, however, the simplified and modified technique suffers from the difficulties that the length of each of the agreed portions of the sequence data would become short if such insertion or deficiency of a gene piece would occur at several discontinuous locations, and that the agreed portions cannot be made continual even if they should otherwise come into agreement. As a result, the involved portion may not be selected as a final candidate and retrieved, even if the sequence portion is actually resembling.

In addition, in the step of assessment for optimization of the optimal disposition to be performed after the selections of the candidate, this simplified technique applies the dynamic programming locally only to the region 93, for example, having approximately sixteen bases before and behind the candidate as an object of retrieval along the diagonal line 92 of the computation matrix 91, as shown in FIG. 9. The problem may arise, however, that the disposition having the total number of about sixteen bases or more of insertion or deficiency may be subject to distortion or deformation and that the two gene sequences are regarded as different from each other even if the key data is replaced with the target data, although they should originally have the same score. On the other hand, this operation presents the advantage that the operation time can become so short because the number of candidates for an operational object can be decreased to a great extent.

Such a modified algorithm is intended mainly to shorten the processing time although some degree of accuracy is sacrificed. Specifically, such a modified algorithm requires for processing as short as about ten and several minutes, while the method for the assessment of the degrees of similarity by executing the dynamic programming requires about ten and several hours to twenty hours for the retrieval time for the process.

A description will be made of the hardware configuration of a conventional system for executing the retrieval of the gene database. First, the basic configuration of the system will be described with reference to FIG. 10 which is a block diagram showing the basic configuration of a gene database retrieval system. As shown in FIG. 10, reference numeral 101 denotes a workstation, reference numeral 102 an external storage device, reference numeral 103 a communications modem, reference numeral 104 a network, and reference numeral 105 a database in a research institution or organization. In this gene database retrieval system, the workstation 101 is a portion functioning as a man-machine interface, which is located on the side of a researcher, and the process for data retrieval (homology retrieval) is executed on the basis of a local gene database.

To the workstation 101 is connected the external storage device 102 working as a gene database. A target data of a gene sequence data is acquired from a recording medium such as a CD-ROM or a hard disk, in which information on the gene sequence data is stored by the external storage device 102. Further, a degree of similarity with respect to a key data of a retrieval key is assessed and the homology retrieval of the gene sequence to be extracted from the target data as a candidate is executed. In addition, the workstation 101 is connected with the database 105 in the research institution or organization as another gene database through the modem 103 and the network 104, thereby enabling information on the gene database to be acquired from the database 105. With the information acquired from the database 105 as a target data, there are executed the process for the data retrieval on the basis of the local gene database and the process for the homology retrieval for the information on the gene sequence data with respect to the key data of the retrieval key.

The sequence data of the gene sequence obtained by experiments and so on is entered into the workstation 101 directly through a keyboard or indirectly through a recording medium such as a floppy disk. With this sequence data as a key data for the retrieval key, the gene database is subjected to a retrieval process (homology retrieval). When the gene database in possession of each researcher is subjected to the retrieval process (homology retrieval), the similar sequence is subjected to the retrieval process (homology retrieval) using the altered and simplified algorithm in the manner as described hereinabove. The entire retrieval process is executed by processing programs described by software. A data distributed in the form of a CD-ROM may be updated in a relatively long time after the previous data has been distributed and an interval of distribution of CD-ROMs may sometimes become too long. For the reasons as described hereinabove, it may in many occasions take a long time to allow researchers to make access to the latest information on the sequence data of the gene sequences analyzed recently. Hence, on many occasions, many researchers make access to a public large-size database organization via public lines through the communications network 104 in order to enable a sure retrieval and subject the gene sequences they have analyzed to final data retrieval in order to determine whether their gene sequences are novel. When they have been found novel as a result of such a final data retrieval, many of them are allowed to be registered as they are.

As described hereinabove, the conventional gene database retrieval system requires the use of a large-scale computer having the processing capacity of computing a very large volume of computation in order to execute dynamic programming. Since such a large-scale computer cannot be utilized so readily for various reasons, it is not easy to subject the gene database to the data retrieval (homology retrieval) so often.

SUMMARY OF THE INVENTION

Therefore, the object of this invention is to provide a gene database retrieval system capable of making a retrieval (homology retrieval) with high accuracy and for a practical processing time that can be shortened compared with the method for the computation using its modified algorithm.

In order to achieve the object, the gene database retrieval system according to the present invention is provided with a dynamic programming operation unit for performing the operation of the dynamic programming as an operation section unit of a hardware circuit for exclusive use. The first feature to be achieved by the gene database retrieval system according to this invention comprises:

a gene database for storing a sequence data of sequences of bases of a nucleic acid and/or sequences of amino acids of a protein, each constituting a gene whose structure has been analyzed and identified;

a dynamic programming operation unit for determining a degree of similarity between a target data and a key data, said target data being constituted by a sequence data of bases from said gene database, and said key data being constituted by a sequence data of bases functioning as a retrieval key; and a central processing device unit for parallel-executing an access process of making access to said gene database, and an operation process of determining the degree of similarity by entering a sequence data of bases one after another from said gene database as the target data by making controls over both of said gene database and said dynamic programming operation unit.

As the second feature residing in the gene database retrieval system according to this invention, the central processing device unit for controlling the dynamic programming operation unit comprises:

a first operation control means for executing an operation for determining the degree of similarity between the target data and the key data by altering the target data one after another with respect to the key data, acquiring the sum value of the sequence data of each target data occurring at the operation, and storing only the maximal sum values for the sequence data;

a second operation control means for classifying the maximal sum values of the sequence data of the target data determined by the first operation control means, and determining the order of the sequence data as an object of extraction; and a third operation control means for performing a re-operation for determining the degree of similarity between the target data and the key data by utilizing the sequence data for the object of extraction as a target data in accordance with the order of the sequence data functioning as the object of extraction, then performing an operation for storing the sum value of the sequence data of the target data occurring at the time of the operation, acquiring a direction selection data created during the operation, and determining the optimal disposition of the sequence data of the target data with respect to the key data.

Further, the gene database retrieval system according to the present invention has the third feature that it is provided with the dynamic programming operation unit comprising:

a key memory for storing the key data of the sequence data of bases, functioning as the retrieval key;

a target memory for storing a target data of the sequence data from the gene database;

a score memory for storing the definition of the degree of similarity between the individual base elements of the sequence data of the bases;

a basic operation processing section for executing a basic operation of the dynamic programming;

a direction selection memory for storing a record of a direction of selecting a locally optimal value occurring at the time when the basic operation processing section performs the basic operation of the dynamic programming;

a sum value memory for storing the sum values obtained by the operation of the dynamic programming; and a control section for controlling the operation of the dynamic programming by controlling each of said memories and said basic operation processing section.

In addition, the fourth feature of the gene database retrieval system according to this invention resides in the dynamic programming operation unit further comprising:

a rewritable score memory for storing a score value of the degree of similarity;

wherein said central processing device unit is arranged in order to execute a process for controlling the operation by the third operation control means by altering a portion or a whole of the score values of the degrees of similarity after having stored the score values of the degree of similarity in said score memory, and to perform a process for controlling the operation by the first operation control means.

Furthermore, the fifth feature of the gene database retrieval system according to this invention resides in the dynamic programming operation unit further comprising:

a rewritable score memory for storing the score values of the degree of similarity and for holding the score values in a non-symmetrical form of a matrix configuration of sequence elements in accordance with sequence elements on the key data side;

wherein said central processing device unit is arranged in order to perform the control of the operation by said first or third operation control means by utilizing the score value of said score memory.

The gene database retrieval system according to this invention further has the sixth feature characterized by the dynamic programming operation unit comprising:

a data conversion section for converting a data type into a predetermined form, wherein the sequence data stored in the gene database is compressed or transformed; and wherein said central processing device unit is arranged in order to execute the operation of the dynamic programming by reading the sequence data of the gene database in an intact form, to transmit the read sequence data to the dynamic programming operation unit and to allow the input sequence data to be converted into a predetermined form by the data conversion section of said dynamic programming operation unit.

Furthermore, the gene database retrieval system according to the present invention has the seventh feature characterized by the dynamic programming operation unit further comprising:

the data conversion section for converting a data type into a predetermined form, wherein the operation of the dynamic programming is executed by reading the sequence data from the gene database, allowing the read sequence data to be compressed or transformed in the central processing device unit, transmitting the compressed or transformed data to the dynamic programming operation unit, and by allowing the data conversion section of said dynamic programming operation unit to convert the data into a predetermined form.

In addition, the gene database retrieval system according to this invention has the eighth feature that resides in that the third operation control means for determining the optimal disposition of the sequence data performs the following operation controls:

an operation for executing the operation for each row until reaching a predetermined length of the key data or the target data;

an operation for acquiring the maximal value of the sum values for each row and for interrupting the operation when the row is found which is identical to the maximal sum value determined by the operation by the first operation control means;

an operation for acquiring the contents of the sum value memory of the involved row and the direction selection data;

an operation for determining the position of the maximal value of the sum values from said sum value memory;

an operation for acquiring the direction selection data corresponding to the position of the maximal value thereof; and an operation for acquiring the direction selection data while re-executing the operation of the dynamic programming on the basis of the direction selection data at least in the position identical to the corresponding position or in one region containing the position or more than the position.

Similarly, the gene database retrieval system according to this invention has the ninth feature characterized in that the third operation control means for determining the optimal disposition of the sequence data performs the following operation controls:

an operation for executing the operation for every column until reaching a predetermined length of the key data or the target data;

an operation for acquiring the maximal value of the sum values for each column and for interrupting the operation when the column is found which is identical to the maximal sum value determined by the operation by the first operation control means;

an operation for acquiring the contents of the sum value memory of the involved column and the direction selection data;

an operation for determining the position of the maximal value of the sum values from said sum value memory;

an operation for acquiring the direction selection data corresponding to the position of the maximal value thereof; and an operation for acquiring the direction selection data while re-executing the operation of the dynamic programming on the basis of the direction selection data at least in the position identical to the corresponding position or in one region containing the position or more than the position.

The tenth feature of the gene database retrieval system according to the present invention resides in the system further comprising a device for determining a gene sequence, which outputs a sequence data of bases for the retrieval key;

wherein the sequence data of the bases output from said device is input as the key data into said dynamic programming operation unit.

Further, the gene database retrieval system according to this invention has the eleventh feature characterized in that the access process for making access to the gene database by said central processing device unit is executed in parallel to the operation process by said dynamic programming operation unit at least for a portion of the time period of the operation of the processes, and wherein said central processing device unit is so arranged as to read the oncoming target data from the gene database prior to the operation by said dynamic programming operation unit during the period of time in which the operation is being executed by said dynamic programming operation unit.

In addition, the gene database retrieval system according to the present invention has the twelfth feature characterized by the dynamic programming operation unit further comprising:

a constant register for storing a constant value for use in comparing the sum values acquired by the operation of said dynamic programming; and an operation element for replacing the sum value with the constant value when the sum value is brought into a given relationship with the constant value of the constant register.

Furthermore, the gene database retrieval system according to this invention is provided with the thirteenth feature characterized by the dynamic programming operation unit further comprising:

a constant register for storing a constant value for use in comparing the sum values acquired by the operation of said dynamic programming; and an operation element for replacing the sum value with the constant value when the sum value is brought into a given relationship with the constant value of the constant register.

As described hereinabove, the gene database retrieval system according to this invention has the basic system configuration which comprises the gene database, the dynamic programming operation unit of the operation section unit for exclusive use, and the central processing device unit. The gene database contains the sequence data of the sequences of the bases of the nucleic acids of genes whose structures have been analyzed and identified, and/or the sequences of the amino acids of proteins so analyzed and identified. The dynamic programming operation unit is arranged in order to execute the operation for determining the degree of similarity between the target data and the key data by utilizing the sequence data of the bases from the gene database as the target data and the sequence data of the bases as the key for retrieval. On the other hand, the central processing unit is so arranged as to parallel operate both of the access process for making access to the gene database and the operation process for determining the degree of similarity by entering the base sequence data one after another from the gene database as the target data by controlling both of the gene database and the dynamic programming operation unit.

The gene database retrieval system according to this invention is provided with the dynamic programming operation unit of the operation section for exclusive use for performing the operation of the dynamic programming, thereby enabling the high-speed execution of the operations for the dynamic programming. Further, as this operation process is arranged in order to be executed parallel to the operations of the access process for making access to the gene database by the central processing device unit, the central processing device unit can execute the access process, for making access to the gene database, for example, for the oncoming target data during the period of time during which the dynamic programming operation unit is executing the operation for determining the degree of similarity for the previous target data. Hence, the gene database retrieval system according to this invention can execute the data retrieval (homology retrieval) for the gene database with a high throughput as a whole.

Further, the gene database retrieval system according to this invention is so arranged as to compute the degree of similarity of the gene sequence by the dynamic programming by controlling the operations by the first operation control means, the second operation control means and the third operation control means when the central processing device unit performs the process for the retrieval of the gene database by utilizing the dynamic programming operation unit, thereby enabling the execution of extraction of the operation for an optimal candidate.

At this end, the first operation control means is arranged in order to execute the operations for determining the degrees of similarity between the target data and the key data by varying the target data with respect to the key data one after another and to store only the maximal sum value among the sum values of the sequence data of each target data occurring at the time of this operation. The second operation control means is arranged in order to classify the maximal sum values for the sequence data of each target data determined by the first operation control means and to determine the order of the sequence data as an object of extraction. On the other hand, the third operation control means is arranged in order to perform the re-operation for determining a degree of similarity between the target data and the key data by utilizing the sequence data for the object of extraction as a target data in accordance with the order of the sequence data functioning as the objects of extraction, then to perform the operation for storing the sum value for the sequence data of each target data occurring at the time of the operation, to acquire the direction selection data created during the operation, and to determine the optimal disposition of the sequence data of the key data with respect to the target data.

As described hereinabove, the gene database retrieval system according to this invention is arranged in order to enter the sequence data of the target data one after another into the dynamic programming operation unit, to determine the degree of similarity of the sequence data of the target data, to hold only the maximal sum value of the degrees of similarity occurring at the time of the operation, and to acquire the maximal sum value corresponding to each target data. Then, the target data is selected on the basis of the maximal sum value. During the operation, only the maximal sum values are transmitted from the dynamic programming operation unit and no unnecessary data is transmitted between the dynamic programming operation unit and the central processing device unit. With this arrangement, the dynamic programming operation unit can execute the operations continually, thereby improving the operation processing speed. Further, as the selection of the target data can be determined on the basis of the maximal sum value acquired by the operations of the dynamic programming, all the candidates to be sustained or left can be selected, unlike the simplified technique as described hereinabove.

In other words, when the optimal disposition is finally acquired, the sum values of the operation matrix and the direction selection data for the back-tracing are required on the side of the central processing device unit. In the initial stage, however, the dynamic programming operation unit computes the degrees of similarity of one entry (target data) extracted from the gene database and generates only the maximal value among the sum values of the degrees of similarity onto the central processing device unit. In the stage in which the maximal values among the sum values of the degrees of similarity of the entries have been determined, the maximal values are classified on the basis of the degree of homology and the dynamic programming operation unit is allowed to compute the degrees of similarity again for only the sequence data having the higher degree of homology. By re-computing the degrees of similarity, all data, including the direction selection data for the back-tracing, for each operation matrix are extracted from the dynamic programming operation unit into the central processing device unit, thereby enabling the operation control to decrease the total amount of data transmission between the dynamic programming operation unit and the central processing device unit to a considerably large extent and shortening the operation time to a great extent.

In addition, the dynamic programming operation unit of the gene database retrieval system according to this invention is provided with the rewritable score memory for storing the score values of the degrees of similarity. The score values stored in the score memory can be altered by the central processing device unit prior to the operation control for each dynamic programming, thereby enabling the candidate to be extracted in the initial stage and the degree of similarity to be assessed by the dynamic programming on the basis of the different standard of assessment for the computation of the degree of similarity, such as the selections of the candidate during the operation.

Furthermore, the dynamic programming operation unit of the gene database retrieval system according to this invention is provided with the data conversion section for converting the data form into the given form. The data conversion section allows the central processing device unit to transmit the sequence data from the gene database in its direct or intact form or in a transformed or compressed form, thereby allowing the dynamic programming operation unit to acquire the sequence data of the gene data in the form converted into its desired form and to execute the operation for the dynamic programming. This arrangement can substantially shorten the time required for data transmission to the dynamic programming operation unit and ultimately shorten the operation time.

More specifically, the processing speed of the dynamic programming operation unit can be usually made higher by raising the degree of parallelism of the operations or by raising the operation speed by utilizing an element operable at a high speed. However, as a bus form of a standard specification is utilized for data transmission between the dynamic programming operation unit and the central processing device unit of this gene database retrieval system, a rate of transmission undergoes some restrictions. For example, a SCSI (Small Computer System Interface) system can make synchronous data transmission at no more than 4 MB per second, while it can make non-synchronous data transmission at no more than 1 MB per second. Further, the rate of transmission is restricted from the point of view of compatibility among devices when a general purpose bus is adopted. This problem with transmission can be solved by transmitting data in a compressed form. As the data expression form for the gene database, there may be generally utilized ASCII codes of a general text form, which are constituted each by eight bits. Although two hundred and fifty six pieces of data can be expressed by eight bite, fifteen kinds of codes are satisfactory for the expression of a DNA so that at least four bits are required as the bit number. Hence, the amount of data transmission can substantially be increased twice simply by packing four bits and transmitting data in an 8-bit code unit. As described hereinabove, the gene database retrieval system according to this invention can transmit data between each of the units at a substantially higher speed by transmitting the data into the dynamic programming operation unit in a form in which the sequence data from the gene database is transformed.

In addition, when the third operation control means for determining the optimal disposition of the sequence data re-computes the degree of similarity, the gene database retrieval system according to this invention is arranged in order to execute the operation for each row of the operation matrix until the operation for each row reaches the predetermined key length and target length, to acquire the maximal value among the sum values for each row thereof, and to suspend the operation when the row of the operation matrix is determined which is agreeable with the maximal value of the sum values determined by the first operation control means. Thereafter, the contents of the sum value memory for that row thereof and the direction selection data are acquired, and the position of the maximal value of the sum values is determined from the sum value memory. In addition, the direction selection data corresponding to the position of the maximal value thereof is acquired, and the direction selection data is further acquired while executing the operation of the dynamic programming again at least in the position identical to the position described beforehand or in one region or more containing the point, on the basis of the previously acquired direction selection data.

By utilizing the maximal sum value determined at the operation by the first operation control means in the manner as described hereinabove, the position in which the maximal sum value for determining the partially optimal disposition can be determined without executing the operations for all the sum values. Further, it is possible to acquire the direction selection data necessary for determining the optimal disposition of the sequence data. This arrangement can also shorten the operation time to a great extent.

Although the operation of each of the sum values is executed in the row direction of the operation matrix in the previous embodiment of this system, it can likewise be executed in the column direction of the operation matrix. In this case, too, the position in which the maximal sum value exists for determining the partially optimal disposition exists can be determined by utilizing the maximal sum value determined by the first operation control means, without executing the operations for all the sum values. This arrangement can likewise shorten the operation time.

Furthermore, the gene database retrieval system according to this invention is provided with a device for determining the gene sequence, which outputs a sequence data of bases as the retrieval key. The sequence data of the bases output from the device for determining the gene sequence is transmitted to the dynamic programming operation unit. With this arrangement, the retrieval for the gene database can be made by utilizing the sequence data output from the device in its intact form as the retrieval key, thereby proceeding with experiments for determining the gene sequence with high efficiency.

Other objects, features and advantages of this invention will become apparent in the course of the description which follows, with reference to the accompanying drawings.

BRIEF DESCRIPTION OF THE DRAWINGS

FIG. 4 is a flow chart showing a process flow for controlling the operation by a central processing device unit of the gene database retrieval system according to an embodiment of this invention.

FIG. 5a is a score table of a non-synchronous score memory at the time of operation execution, in which a score value with respect to "N" on the target side is altered to "0", and FIG. 5b is a table showing data of a sum value memory and a direction selection memory for the results of operation.

FIG. 10 is a block diagram showing a basic system configuration of a conventional gene database retrieval system.

DESCRIPTION OF THE PREFERRED EMBODIMENTS

Figure 1:
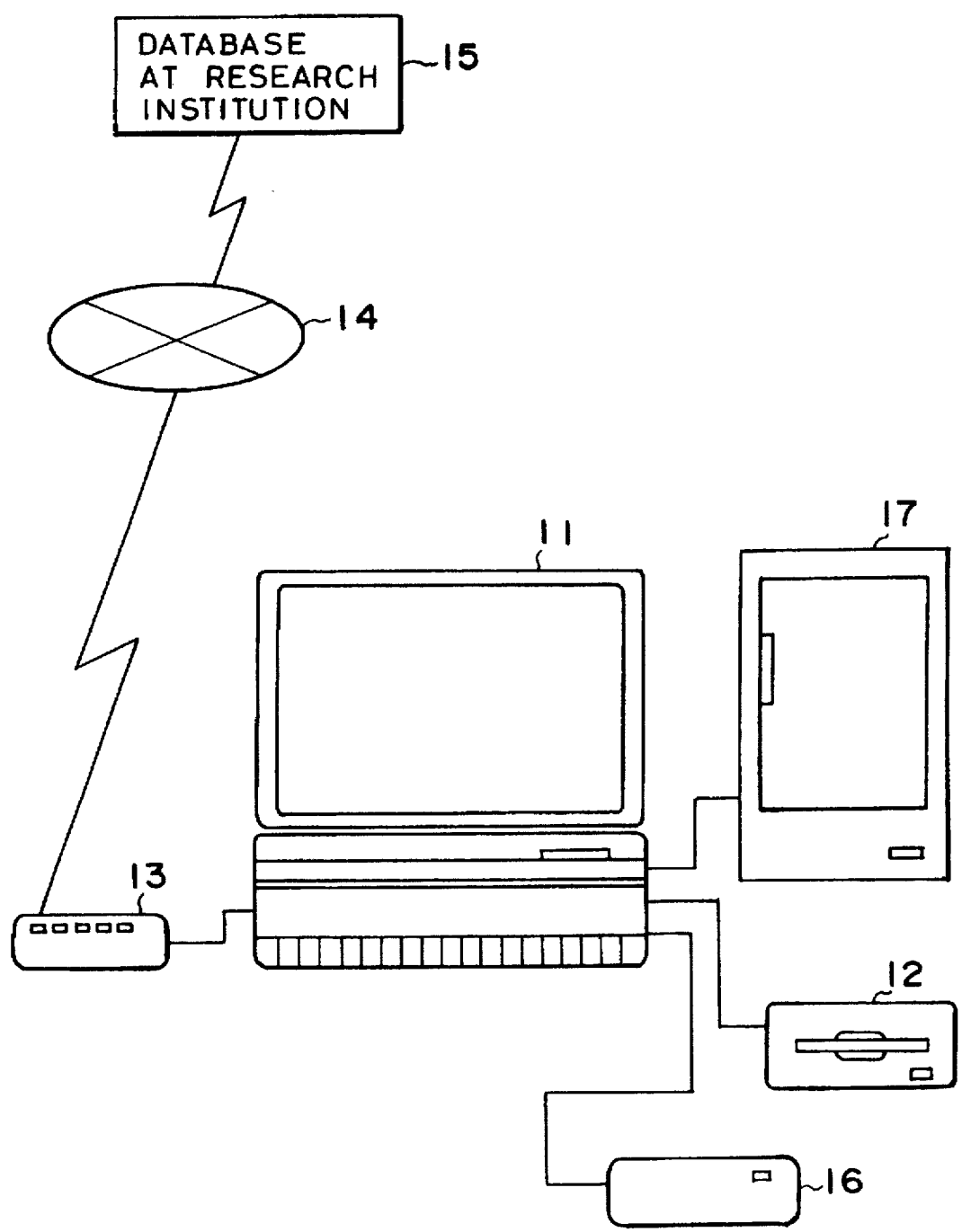
FIG. 1 is a block diagram showing a whole device configuration of the gene database retrieval system according to an embodiment of this invention.

The present invention will be described in more detail by way of examples with reference to the accompanying drawings. FIG. 1 is a block diagram showing the whole device configuration of the gene database retrieval system according to this invention, in which reference numeral 11 denotes a central processing device unit (or a work-station), reference numeral 12 denotes an external recording medium device unit (hereinafter referred to sometimes as "external recording medium"), reference numeral 13 denotes a communications modem, reference numeral 14 denotes a public communications network, reference numeral 15 denotes an external database system, reference numeral 16 denotes a dynamic programming operation unit (hereinafter referred to sometimes as "operation unit"), and reference numeral 17 denotes a device or sequencer for automatically determining sequences of bases of nucleic acids.

First, a description will be made of the configuration of each of the devices and units constituting the system with reference to FIG. 1. The central processing device unit 11 is provided with the control functions of the system as a whole and with the processing functions of a man-machine interface. To the central processing device unit 11 are connected the operation unit 16 for determining a degree of similarity of gene sequences, the external recording medium 12 for storing a data of gene sequences as a gene database, the automated sequencer 17 for creating a sequence data as a retrieval key, and the communications modem 13, which are connected with each other through a data bus by a data transmission system (a bus system) of a given interface.

In the gene database retrieval system according to the embodiment of this invention, a SCSI (Small Computer System Interface) bus is employed for an interface connecting the operation unit 16 and the central processing device unit 11, and for connecting the external recording medium 12 of the gene database and the central processing device unit 11. In this case, the operation unit 16 may be connected through an interface of a local area network type such as Ethernet or the like, or through an internal bus system as will be described hereinafter in another embodiment of this invention. When the connection is made through the internal bus system, the transmission rate of data can be maintained at a high level and a decrease in throughput due to the restraint of the data transmission speed can be avoided. As the external recording medium 12 working as the gene database in this embodiment of the invention, for example, there may be employed CD-ROMs, hard disks, optic-magnetic disks and so on.

The device or sequencer 17 for automatically determining the sequences of the bases of the nucleic acids is so arranged as to output the key data of a gene sequence of the retrieval key and to input the sequence data of the key data into the central processing device unit 11. In the system configuration according to this embodiment of the invention, the device or sequencer 17 is connected with the central processing device unit 11 through a GPIB interface (General Purpose Interface Bus: IEEE 488). The system configuration of the device or sequencer 17 may be the one described, for example, in Japanese Unexamined Patent Publication Kokai No. 61-62,843 and a detailed description thereof will be omitted for brevity of explanation. As the device for generating the sequence data of the key data acting as the retrieval key, there may be employed a device for determining a sequence of bases of an amino acid, a digitizer or an image scanner for reading a sequence of bases thereof, for example, by utilizing an X-ray film. Further, it is possible to input the retrieval key data directly from keyboard, in place of the such a device.

The communications modem 13 is connected with the central processing device unit 11 in order to make the retrieval for a gene data, for example, from the external database 15 at a research institution or organization remote from the location at which the retrieval is being performed. More specifically, the communications modem 13 is connected with the public communications network 14 through which the central processing device unit 11 is connected with the database institution or organization. Although a modem for analog circuit for transmitting audio signals converted from digital signals is utilized in this embodiment of the system as described hereinabove, it is possible to employ a digital circuit through a terminal for exclusive use.

Figure 2:
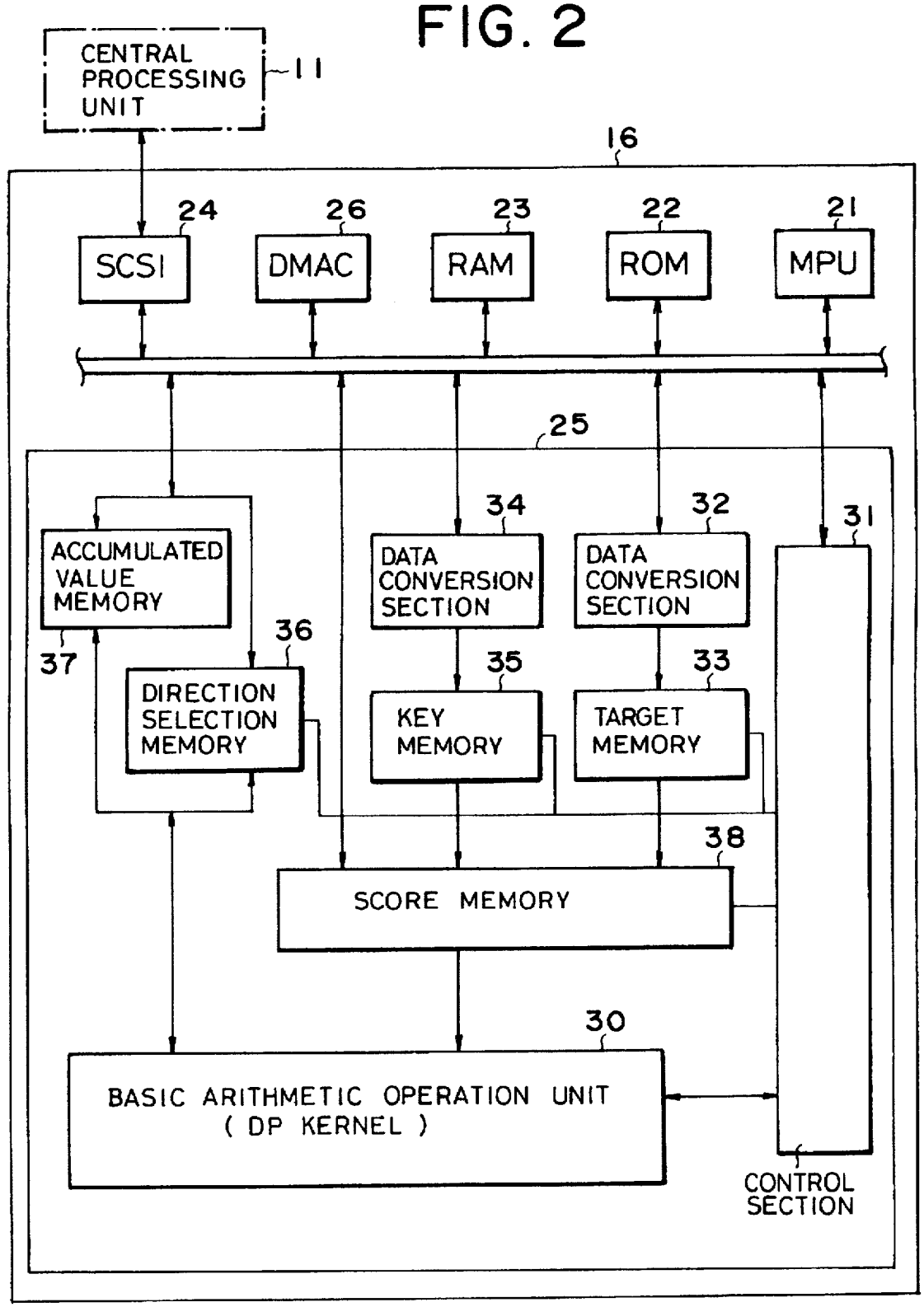
FIG. 2 is a block diagram showing the configuration of a dynamic programming operation unit of the gene database retrieval system according to an embodiment of this invention.

A description will now be made of the system configuration of the operation unit 16 with reference to FIG. 2 showing a block diagram indicative of the system configuration of the dynamic programming operation unit. As shown in FIG. 2, the dynamic programming operation unit 16 comprises a microprocessor 21 for controlling the entire system of the operation unit, a program memory 22 of Read-Only Memory (ROM) for storing an operating system, a work memory (RAM) 23 for storing a transmission data, a DMA controller 26 for executing a direct memory access (DMA) transmission for a transmission data of the memory, a SCSI controller 24 for the interface with the central processing device unit 11, and an operation processing section 25 for executing the operation of the dynamic programming.

The operation processing section 25 of the operation unit 16 is constituted by an operation circuit section for exclusive use, which allows a hardware logic circuit to execute the operations of the dynamic programming. Hence, the operation processing section 25 may comprise processing elements including a first data conversion section 32 and a second data conversion section 33, each for converting the transmitted data into a given data form, a control section 31 for performing operation controls by the operation processing section, such as a timing of the operation and the like, a key memory 35 for storing the key data, a target memory 33 for storing the target data, a score memory 38 for storing scores for the operations of the dynamic programming, a sum (accumulated) value memory 37 for storing sum values of intermediate results of the operations, a direction selection memory 36 for storing direction selection data of the intermediate results of the operation, and a basic operation section (arithmetic operation unit; DP kernel) 30 for executing the basic operation of the dynamic programming. These processing elements are connected and disposed so as to hold a relationship in position with each other, thereby enabling the data to flow in a smooth fashion.

The configuration of the data width of each processing element in the circuit configuration of the operation processing section 25 is: 32 k×8 bits for each of the key memory 35 and the target memory 33; four sets of 64 k×8 bits for the score memory 38 (the DP kernel of the basic operation section being of configuration with four operation LSIs); 32 k×16 bits for the sum value memory 37; and 32 k×4 bits for the direction selection memory 36.

The operation unit 16 is arranged in order to execute the operation on the basis of an operating parameter and a data transmitted via the SCSI interface from the central processing device unit 11. The operation parameters designate the operating mode selections, such as a "block/single" operation selection, a "row/column" operation selection, a "maximal/minimal" operation selection, and the like, and set a score table for the computation of the degree of similarity at the time of the execution of the operation. When the block operation is designated by the operation mode from the "block/single" operation selections, the operation for each element of the operation matrix in the designated region is executed continually and comprehensively. On the other hand, when the single operation is designated by the operation mode from the "block/single" operation selections, the operation for each element of the operation matrix is executed one row or column after another. The operation mode from the "row/column" operation selections designates the operation in the row direction or the column direction. The operation mode from the "maximal/minimal" operation selections makes the MAX or MIN designation of the recurrence formula at the time of the operation of the dynamic programming.

The designation data of the operation parameters is set via the microprocessor 21 in the control section 31 and the basic operation section 30 of the operation processing section 25, and the operation controls are performed by the operation mode. At the time when the operation is to be executed, the score values are written in the score memory 38, the sequence data acting as the retrieval key is written in the key memory 35, and the sequence data of the target data is written in the target memory 33.

As the command for the start of the operation is transmitted from the central processing device unit 11 to the operation unit 16, the microprocessor 21 makes a decision on the transmission of this command and transmits a signal indicative of the start of operation to the control section 31. The control section 31 is provided with an address creation circuit (not shown) of 15 bits, comprised of a counter, which creates addresses for the key memory 35 and the target memory 33 and reads the data transmitted to the addresses one after another. When the operation is designated in a "row" mode of the operation in the row direction by the "row/column" operation selection, a counter of the memory (the key memory in this example) counts up the data in the row direction, and the address of the memory (the target memory in this example) on the column side is increased by one increment, when the operation has been executed up to the designated address. On the other hand, when the operation is designated in a "column" mode of the operation in the column direction, the counter of the memory likewise counts up the data in the column direction, and the address of the memory on the row side is increased by one increment when the operation has advanced up to the designated address.

Each of the key data read from the key memory 35 and the target data read from the target memory 33 by the designation of each of the addresses from the control section 31 is combined simply with each other to comprise 16 bits. The combined data is transmitted to the score memory 38 as an address and the score value is read from the score memory 38. The read score value is then transmitted to the basic operation section 30 that executes the basic operation for the dynamic programming on the basis of the data from each of the score memory 38, the sum value memory 37 and the direction selection memory 36, and the results of operation are stored again in the sum value memory 37 and the direction selection memory 36. Each of the sum value memory 37 and the direction selection memory 36 is of a two-sided configuration and is employed for reference to the results of operation and storage thereof as if a seesaw. If overflow would occur during operation, a signal indicative of overflow is transmitted to the control section 31, thereby suspending the operation and transmitting a signal indicative of interrupt into the microprocessor 21. When the operation is being executed in a single operation mode by the designation from the "single/block" operation selections, the operation process is caused to be suspended in each row or column. With this arrangement, data can be rewritten while reference is made, for example, to the contents of the sum value memory.

Figure 3:
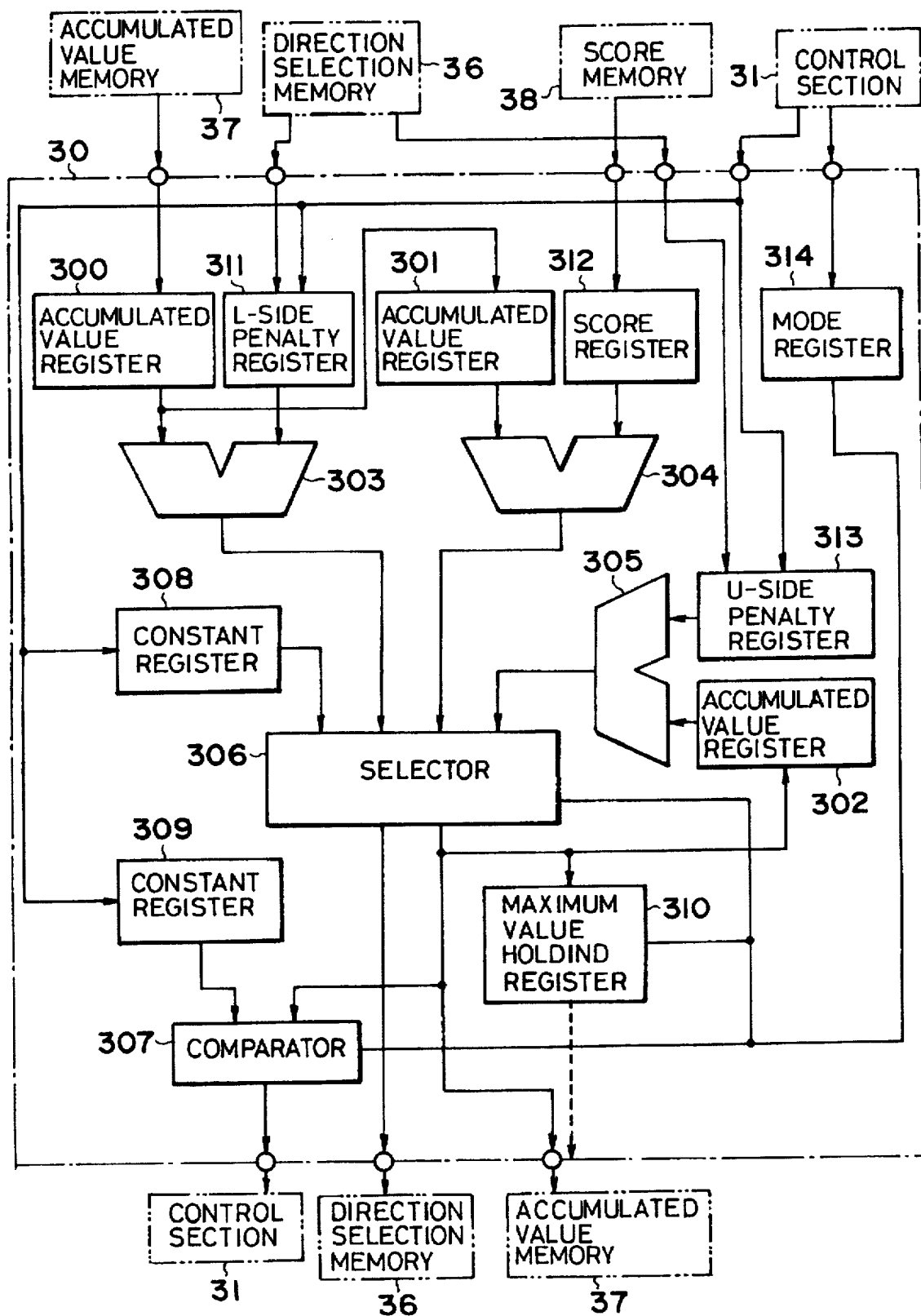
FIG. 3 is a block diagram showing a circuit configuration of the operation LSIs constituting elements of a basic operation processing section of the gene database retrieval system according to an embodiment of this invention.

Next, a description will be made of the configuration of the basic operation processing section 30 of the operation processing section 25 of the operation unit 16. FIG. 3 is a block diagram showing the circuit configuration of the operation LSIs constituting the basic operation processing section. The basic operation processing section 30 is constituted by four operation LSIs, and FIG. 3 shows the circuit configuration of one of the operation LSIs. As each of the four operation LSIs can execute the operation independently and separately from the rest, each of the operations can be executed in a parallel fashion. As shown in FIG. 3, each of the operation LSIs comprises sum (accumulated) value registers 300–302, adders 303–305, selector 306, comparator 307, constant registers 308–309, maximal value holding register 310, L-side penalty register 311, score register 312, U-side penalty register 313, and mode register 314.

Each of the operation LSIs of the basic operation processing section 30 is of such a configuration that data at D(i, j−1) only can be input as a sum value data from the outside in order to reduce the number of input-output pins to the least possible number and so on and to be operable at a high speed. The data at D(i−1, j−1) and D(i−1, j) are set by internal transmission processing. In other words, the data at D(i, j−1) only is input from the outside to the sum value register 300 for storing D(i, j−1), and this data is also employed by the internal transmission processing as D(i−1, j−1) to be employed in the oncoming operation cycle.

The data D(i, j−1) utilized in the operation cycle in the immediately preceding position and stored in the sum value register 300 is transmitted by the internal transmission process to the sum value register 301 in the operation cycle in the position that follows, and it in turn is utilized as D(i−1, j−1). On the other hand, data D(i, j), acquired finally as the results of operation in the operation cycle in the previous position, is transmitted to the sum value register 302 in the operation cycle in the position that follows, and it in turn is utilized for the rest, D(i−1, j−1). With this arrangement, the data D(i, j−1), D(i−1, j−1) and D(i−1, j) are set one after another in the sum value registers 300, 301 and 302, respectively, in the operation cycles in the corresponding positions, which are proceeding in the column direction.

When the result of operation obtained from each of the adders 303–305 by computing the score value of each path and the data from the constant register 308 are input, the selector 306 selects the largest input data and then outputs it. The constant register 308 is employed for cutting back the sum values in a manner as will be described hereinafter. The comparator 307 is arranged in order to output a signal indicative of the suspension of operation to the outside when it is found as a result of comparison that the largest sum value among the sum values output from the selector 306 agrees with the data set in the constant register 309 or that the data of the sum value is larger than the data set therein. This signal can effectively be employed in a manner as will be described hereinafter, when the operation is to be suspended at an optional sum value during the execution of the operation of the dynamic programming.

The maximal value holding register 310 has the function of re-storing the larger data as a result of constant comparison between the data output from the selector 306 and the data held thereby. With this arrangement, the maximal value holding register 310 is sustained in such a state as the largest data among the data output from the selector 306 is always held until the system is reset.

The score register 312 is so arranged as to input the score value from the outside on the basis of the score table in regard to agreement of one element of the sequence data with another or substitution of one for another. The L-side penalty register 311 and the U-side penalty register 313 are each a register for setting a score for the subtraction of a decrement from the previous score value due to insertion of a gene segment into the gene sequence or deficiency of the gene segment from the gene sequence. When a degree of similarity of the gene data is to be assessed, a larger score (as high as 6 points in this example) is to be subtracted from the score value for the first occurrence of insertion or deficiency, and a smaller score (as low as 4 points) is to be subtracted therefrom for an insertion or deficiency which continually occurs for the second time or more. Hence, the penalty registers 311 and 313 are arranged in such a manner that each of them can hold two values as the score value for insertion or deficiency: one value for the first occurrence of insertion or deficiency and the other value for the subsequent occurrence thereof. The data for determining if the insertion or deficiency is the first one is employed by shifting the data acquired from the data of the direction selection memory (36: FIG. 2). In other words, the score values to be subtracted in each of the L-side penalty register 311 and the U-side penalty register 313 can be shifted by utilizing the direction selection data acquired by the operation implemented in the previous row or column.

During the block operation, the data indicative of the result of operation (i.e. the sum value data to be output from the selector 306 and the direction selection data giving an instruction of the selection bus) is transmitted to the next operation LSI cascade-connected to the first LSI and the final result (the output of the first operation LSI at the time of the single operation) is stored, i.e. the sum value data is stored in the sum value memory 37 and the direction selection data designating the selected bus is stored in the direction selection memory 36.

It is to be noted that, although the basic operation processing section 30 in this embodiment as described hereinabove is so arranged as to execute the operations in order to make the selections of the maximal values, all the operations of the comparator 307, the selector 306 and the maximal value holding register 310 can be arranged so as to select the minimal values by changing the settings of the mode register 314. With this arrangement, the operation of the dynamic programming can be changed in order to determine the optimal bus on the basis of the minimal values of the sum values. The circuit configuration of the basic operation processing section 30 is comprised of a hardware logic LSI circuit that can execute one basic operation of the dynamic programming (the operation of a sequence element of an operation matrix) at an operation speed of approximately 50 ns. Further, in order to improve a comprehensive execution speed, each of the operational LSIs for the basic operation is connected via pipe lines on the circuit configuration. In addition, the operation speed is made further higher by configuring the LSIs with a high-speed semiconductor device.

Next, a description is made of the flow of the operation process for the homology retrieval of the gene data, which is executed by controlling the operations by the dynamic programming operation unit in the manner as described hereinabove. This operation process is executed with the central processing device unit 11 by executing the operation control over the dynamic programming operation unit 16. FIG. 4 is the flow chart for describing the process flow for the operation control in the central processing device unit of the gene database retrieval system. An example of the whole operation in usual use will be described with reference to FIG. 4. The whole process flow comprises the step of setting a key data in the initial stage of setting data (step 41), the step of computing the degree of similarity for each target data in the first stage (step 42), the step of selecting the sequence data of the object by classifying the degree of similarity in the second stage (step 43), and the step of computing the optimal disposition for the selected sequence data in the third stage (step 44). The operation control in the respective stages is made by a first operation control means, a second operation control means and a third operation control means in the central processing device unit 11.

First, a description is made of the execution of the operation of the degree of similarity for the target data in the first stage by the first operation control means. The process in the first stage comprises setting an operation mode of the operation unit 16, setting a score table of the score memory, and computing the maximal value of the sum values for each target data.

In the setting of the operation mode, the operation unit 16 is set to the block operation mode. In the block operation mode, only an intermediate data required for the operation of the next row or column for the given key data and target data is left in a memory area of the operation unit 16, and the continual operation is executed without transmitting the intermediate data to the central processing device unit 11. The setting in this manner allows the operation unit 16 to proceed with the continual operation separately and independently from the central processing device unit 11.

Further, the sum value is replaced with "0", for example, when the score value becomes a negative sum value, in order that the sum value is not caused to be decreased to a great extent by the discrepancy at the portions of the sequence elements between the key data and the target data and as a consequence that the sum value is also caused to be decreased at the subsequent portions of the sequence elements where the key data agrees with the target data. At this end, the constant register 308 of the basic operation processing section 30 sets its cutback value "0" as a constant value, provided that the constant register 308 is so arranged as to set an optional value in accordance with operation conditions.

Figures 8, 9:
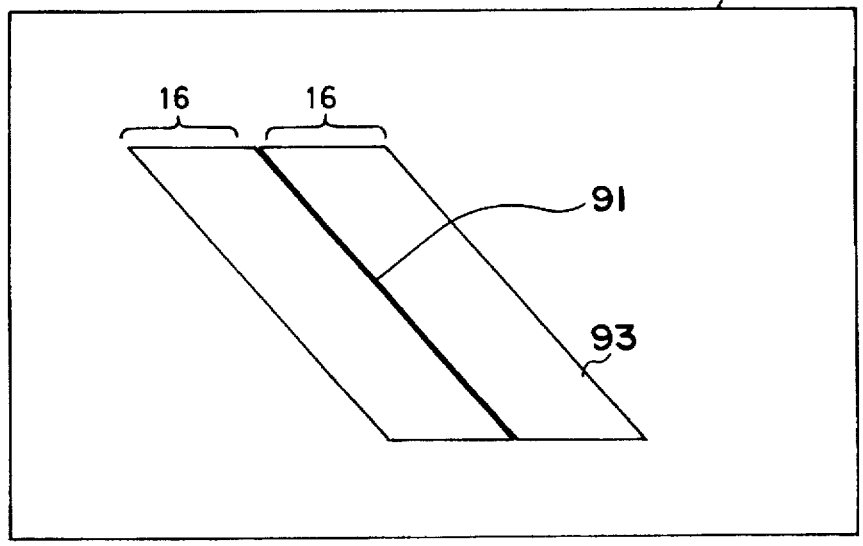
FIG. 8 is a score table showing degrees of similarity to be employed for the gene database retrieval made by utilizing the dynamic programming.
FIG. 9 is a schematic representation showing the operation procedure for the dynamic programming by utilizing an algorithm altered by a simplified technique.

Thereafter, the score table is set in the score memory. The setting of the score table is made by setting an optional score value so as to correspond to a candidate to be extracted as a condition for retrieval. The score values to be employed herein are in principle those, for example, as indicated in the score table as shown in FIG. 8. In the score table, a score value of two points is provided for a combination of a base code, as referred to as "N", indicative of an unidentified base, with base codes, as referred to as "A", "C", "G" and "T", indicative of the corresponding identified bases. Therefore, for example, in the event where a sequence having a consecutive row of three hundred of unidentified bases, as referred to as "N", is registered in a database as it is, like a gene database in which sequence data read, for example, by a device or sequencer for determining sequences of bases of nucleic acids, are registered, such a sequence is retrieved in many cases as noise under some retrieval condition in the case where the length of the key data is almost the same as that of the target data. Accordingly, the score table to be utilized herein is arranged in such a manner as indicated in FIG. 5a that the score value is set to "0" only for the portion of the combination with the unidentified base code, as referred to as "N", on the target data side, so as to become unsymmetrical with the score value for the unidentified base code "N" on the key data side. This setting can prevent a long sequence having unidentified bases "N" from causing noise.

The process that follows from the process of setting the score table is to send the key data and the target data. The key data may include, for example, a sequence data input, e.g. from the device or sequencer 17 for determining sequences of the bases of the nucleic acids, in the manner as described hereinabove, a sequence data assumed from the result obtained by another experiment, or the like. The central processing unit 12 reads the target data one after another from the external recording medium 12 as a gene database or from the external database system 15 through the communications modem 13 and the network 14, and sends it to the dynamic programming operation unit 16. The key data and the target data, sent to the dynamic programming operation unit 16, are written in the key memory 35 and the target memory 33 via the second data conversion part 34 and the first data conversion part 32, respectively, under management of the microprocessor 21.

Each of the first data conversion part 32 and the second data conversion part 32 is adapted to make a data conversion so as to allow data of various expression types acquired from the gene database to comply with a format for an internal process. The data conversion method may comprise writing the converted data in advance in the memory address corresponding to the data prior to conversion and making access to the memory. Further, for example, data packaged in a given type is sent from the central processing device unit 11 and the data is then converted into a data format of its original type by the data conversion part. In this case, the transmission rate by the SCSI bus can be improved equivalently.

Then, the operation is started by sending the command of starting the execution of the operation to the operation unit 16. The microprocessor 21 of the operation unit 16 sends to the control section 31 a signal indicative of the start of the operation. Once the operation is allowed to start, the SCSI bus between the operation unit 16 and the central processing device unit 11 is brought into a released state. Once the SCSI bus is released, the central processing device unit 11 starts reading the next target data by the access process of making access to the external recording medium 12. On the other hand, after the operation has been terminated, the microprocessor 21 of the operation unit monitors the status of the SCSI bus and confirms that the SCSI bus is in a non-use state, followed by the issuance of a service call stating the termination of the operation to the central processing device unit 11.

As soon as the target data has been read by the access process of making access to the external recording medium 12, the central processing device unit 11 then makes access to the operation unit 16, thereby reading and storing the maximal value of the sum values of the results of operation (i.e. the data stored in the maximal value holding register 310). Thereafter, the next new target data is sent to the operation unit 16 and the operation is executed in the same manner. This operation is repeated until no involved target data exists any more in the gene database of the external recording medium 12. At the time of the termination of the operation controls in the first stage, the maximal value of the sum values is stored so as to correspond to all the data entered into the gene database. Further, when the homology retrieval has been made for the new key data, the result of the homology retrieval is stored together with conditions of the retrieval range of the gene database, thereby improving efficiency of retrieval by restricting the retrieval range at the time of the next data retrieval and grouping the data with ease by the degree of similarity between the registered data or the owned data.

Next, a description will be made of the process of making selections in the second stage by the second operation control section. In the selections of a candidate acting as an object of extraction, the maximal values of the degrees of similarity corresponding to each of the target data obtained in the first stage are classified and they are displayed in the order of higher degrees of similarity. After the display of the maximal values, the conditions of the sequence data (target data) on the database side for which the optimal disposition is given are specified in response to an instruction from the user.

Next, the process in the third stage by the third operation control section will be described. In the process in the third stage, the target data is read one after another from the gene database and sent to the operation unit 16 for the target data selected in accordance with the order of the higher maximal sum values by the process in the second stage. Then, the operation of the dynamic programming is re-executed, operations of the degree of similarity between the target data and the key data are made by utilizing the objective sequence data as a target data, and operations are made for storing the sum values of the sequence data of each target data occurring at the time of operation, thereby acquiring the direction selection data created during the operation. Thereafter, a "back-tracing" process is executed on the basis of the direction selection data and the optimal disposition of the sequence data is obtained for the sequence data of the key data.

In the operation for obtaining the optimal disposition of the sequence data, the operation procedures may be implemented in a manner as will be described hereinafter, by using the maximal value of the target data obtained previously. The operation procedures may involve setting the operation unit 16 to the single operation mode, reading the sum value data of the results of operation and the direction selection data one row or column after another and sending them to the side of the central processing device unit 11, and developing the sequences of the whole sum value data and the sequences of the direction selection data on the memory in the central processing unit. After the coordinates of the maximal value of the sum value data have been obtained, the "back-tracing" process may be implemented from the coordinates on the basis of the direction selection data. This method, however, requires a large memory area to be ensured in the operation unit 16 or the central processing device unit 11 when the key data of a large sequence data is combined with the target data thereof, because, given the settings of the lengths of the sequence data to M and N, respectively, the memory area corresponding to the M×N multiplication of sequences is required for each of the sum value data and the direction selection data.

Therefore, in this embodiment according to the present invention, the procedures are adopted, which comprise setting the basic operation section (DP kernel) 30 for the operation of the dynamic programming to the block operation mode in substantially the same manner as in the operation at the first stage and setting the constant for cutting back the operation to the constant register 309. When the constant for cutting back the operation is set to the constant register 309, the constant is always compared with the sum value from the selector 306 by the comparator 307. When the constant is equal to or exceeds the sum value, a signal indicative of the termination of the operation is sent to the control section 31, thereby forcing the computation to be suspended. Therefore, the maximal value of the sum values for each target data given in the first stage is compared to the constant for cutting back the operation, followed by the process of returning the set value of the score table to its original value. It is to be noted herein that, in this case, the score values set in the score table in the score memory are returned to the values as indicated in FIG. 8. When the score values of the score table used for the operation in the first stage are altered in the non-synchronous manner as indicated in FIG. 5a, they are returned to their original values at this stage because no noise to be caused by, for example, a consecutive row of unidentified bases "N", is contained in the sequence selected as candidates for the homology retrieval.

Then, the first data of the target data selected by the operation in the second stage is set and the computation of the degree of similarity is re-executed. In this operation, the key data is not required to be set again because the same data has been used as an object from the operation in the first stage. Although the operation is executed in the operation unit 16 in substantially the same manner as the operation in the first stage, the operation is terminated on the row or column in which the target data agrees with the maximal value because the maximal value of the sum values are set for the involved target data as the constant for cutting back the operation.

As the operation has been terminated, an interrupt signal is issued to the microprocessor 21. After it has received the interrupt signal, the microprocessor 21 is operated to determine the position in which the maximal sum value of the operation matrix exists, with reference to the data left on the last row or column in the sum value memory 37. From the position of the maximal sum value of the operation matrix, the final point of the partially optimal disposition is determined. Further, the direction selection data is acquired from the direction selection memory 36 and the "back-tracing" actions for tracing the paths in the backward direction are implemented from the final position on the basis of the direction selection data. FIG. 5b indicates a specific example of the sum value and the direction selection data of the operation matrix obtained in the manner as described hereinabove. In FIG. 5b, the path of the selection route is indicated by the broken line and the optimal disposition is determined by tracing the selection path in the backward direction from the position of the partially optimal disposition on the basis of the direction selection data. The path along which the trace is implemented in the backward direction is indicated by the solid arrows in FIG. 5b. As shown in FIG. 5b, for example, the sequence "AGC-AGC" of the target data is given for the key data having the sequence "AGCTAGC" as the partially optimal disposition.

When the optimal disposition is determined by the method as described hereinabove, the selected path is traced in the backward direction on the basis of the direction selection data by narrowing the operation range from the position in which the final point of the partially optimal disposition was given and the partially optimal disposition is given up to the position in which the sum value is replaced with the value for cutting back the operation, set in the constant register 308. In order to determine the optimal disposition as a whole, the back-tracing operations are to be implemented in substantially the same manner from the final point of the operation matrix. This method requires only the direction selection data to be stored so that the system according to this invention is required to set the memory having a capacity corresponding to the number of the row of the longer sequence of the target data and the key data.

Furthermore, it is noted in the embodiment of this invention as described hereinabove that the back-tracing operation is implemented on every row or column. It is also possible to acquire the sum value and the direction selection data by tracing the selected paths in the backward direction on every row within the diagonal range, as indicated in FIG. 9. In other words, the sum values are subjected to block operation in the area which is arranged so as to be reduced by the row number "n" larger than one row and the rest of the "n" rows are subjected to the operation at the single operation mode, thereby implementing the operation on every row and acquiring the sum values and the direction selection data of the range along the generally diagonal direction. This method can execute the operation in a balanced manner between the necessary memory amount and the execution time.

Figure 6:
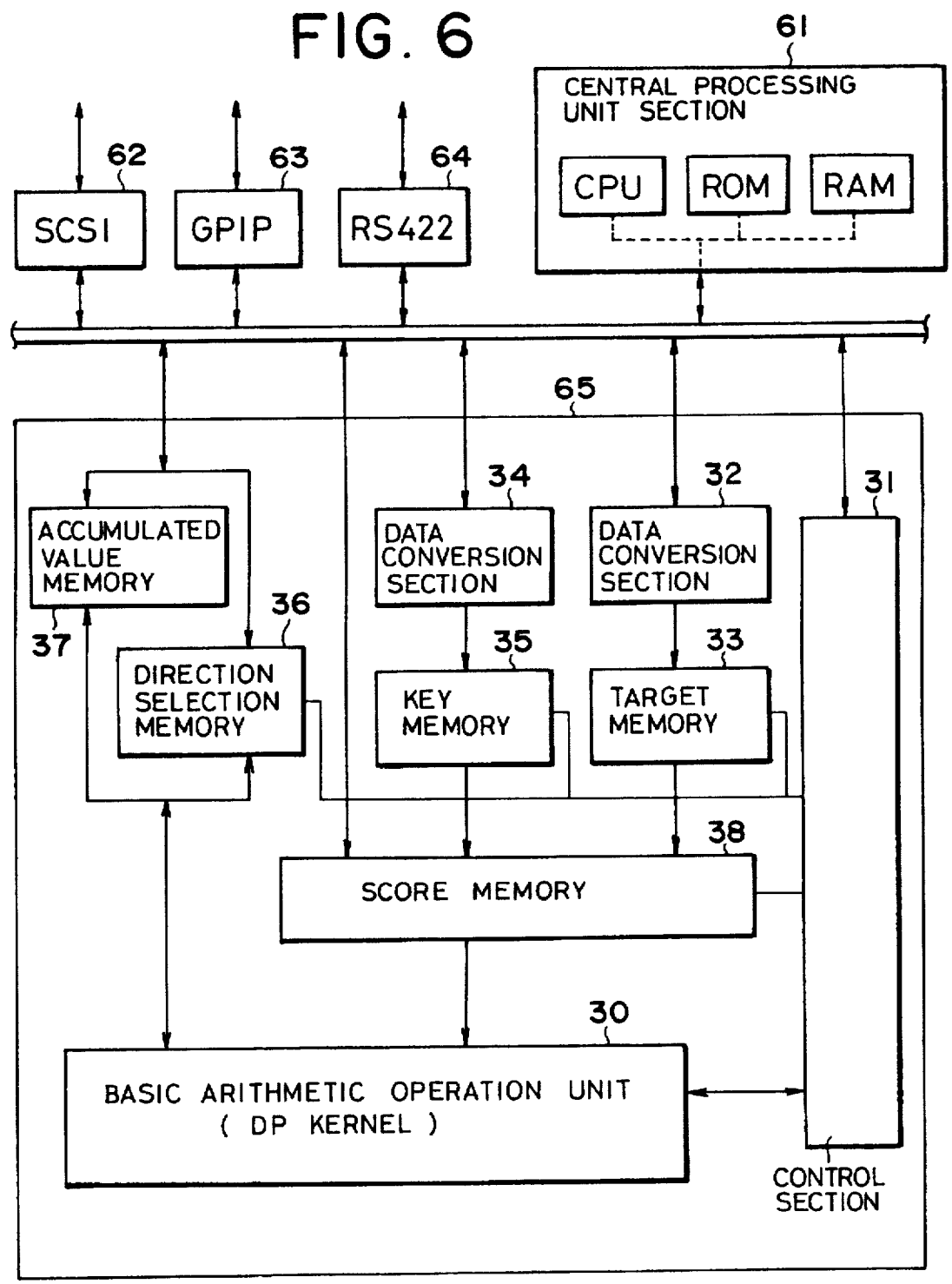
FIG. 6 is a block diagram showing mainly the configuration of an operation processing board of a type in which an operation section for the operation of the dynamic programming is connected directly to an internal bus.
Figure 7A:
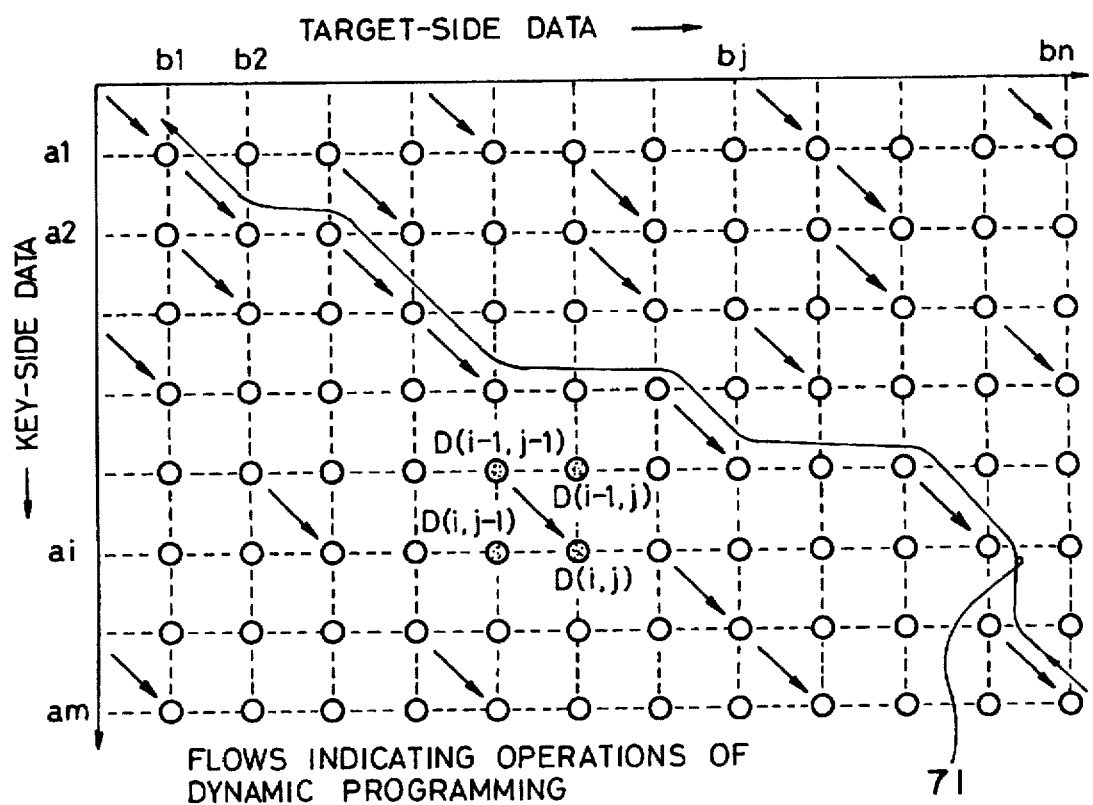
FIG. 7a is a schematic representation showing the whole processing flow of the dynamic programming for computing the degree of similarity.
Figure 7B:
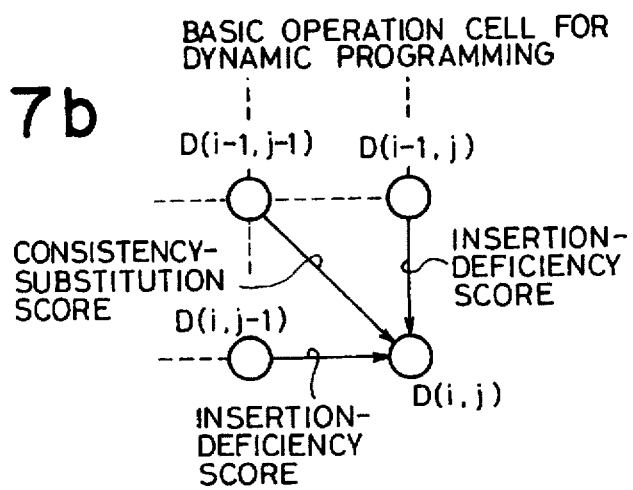
FIG. 7b is a schematic representation showing the operation principle in a basic operation cell for the dynamic programming.

Now, a description will be made of another embodiment of this invention, in which the operation processing section 25 in the operation unit 16 as an operation board is connected directly with the internal bus of the workstation, i.e. the central processing device unit. FIG. 6 is the block diagram indicating mainly the configuration of the operation board of a type in which the operation section for implementing the operation for the dynamic programming is connected directly with the internal bus. As shown in FIG. 6, a block of the same process elements as indicated in FIG. 2 is provided with the same reference numerals. In the embodiment of the type of connecting the operation section directly with the internal bus of the central processing device unit, the data transmission of the operation processing board 65 is executed directly through the internal bus, thereby requiring no system for the interface process to be connected through the SCSI bus, such as the microprocessor, DMA controller, ROM, RAM, SCSI controller and so on.

The process of the data transmission of the data input into and output from the operation processing section (operation processing board 65) is implemented by the process elements of the CPU, ROM and RAM of the central processing device part 61 constituting the main part of the central processing device unit. In this system configuration, the operation processing section 25 in the operation unit is of a structure such that it is connected as the operation processing board 65 directly to the internal bus of the workstation, i.e. the central processing device unit, so that ready access can be made from the CPU constituting the main part of the central processing device unit to the key memory, the target memory and the like.

At the time of the execution of the operation of the dynamic programming, as each of the key memory, the target memory, the score memory and so on is operated in the same manner as in the above-stated embodiment of this invention, in the state in which the operation processing section in the operation unit is disconnected from the internal bus of the CPU of the main part of the central processing device unit, the read process of the next target data can be implemented concurrently with and in parallel to the access process. As the bit width of the data transmission can readily be expanded, for example, to 32 bits for the operation processing section of the type in which it is connected directly from the internal bus of the CPU of the central processing device unit, the speed of the data transmission to the operation processing board 65 can be improved and a space of the whole system can be saved because it is of an on-board type.

Now, a description will be made of a specific example in which the operation time for the homology retrieval is shortened to a great extent by the disposition of the operation processing section for exclusive use. By using the system configuration in which the operation processing board with the DP kernel consisting of four operation LSIs constituting the basic operation section as described in FIG. 3 is loaded in a personal computer, this system took about fifteen minutes for retrieval of about 70,000 entries of GenBank by utilizing the length of the key data of 250 bases. This time period contains all the time required for retrieval for such a large amount of entries, including the access time to a database such as a CD-ROM. As a result, it is found that this time period is shortened to approximately one sixtieth the operation time, i.e. from about ten and several hours to twenty hours, required by a conventional workstation.

In the foregoing description, it is found that the gene database retrieval system according to the embodiment of this invention has the system configuration comprising the gene database, the dynamic programming operation unit and the central processing device unit, wherein the central processing device unit is arranged in order to control the gene database and the dynamic programming operation unit, and to make operations for the access process to make access to the gene database in parallel to the operation process for determining the degree of similarity of the base sequence data input one after another from the gene database into the dynamic programming operation unit. In other words, the dynamic programming operation unit of the exclusive operation unit for the operations of the dynamic programming can execute the operations of the dynamic programming at a high speed in parallel to the operations associated with the central processing device unit. For example, the access process for making access to the next new target data in the gene database can be executed by the central processing device unit during the operations for determining the degree of similarity of the target data by the dynamic programming operation unit. As a consequence, the data retrieval by means of the homology retrieval for the gene database can be performed at a high throughput as a whole.

In the operations by the dynamic programming to be made with the dynamic programming operation, the first stage operation comprises performing the operation for determining the degree of similarity between the target data and the key data by varying the target data one after another with respect to the key data, and storing the maximal sum values for the sequence data of each of the target data occurring at the time of the operation; the second stage operation comprises classifying the maximal sum values of the sequence data for each of the target data determined in the first stage operation and determining the order of the sequence data as an object of extraction; and the third stage operation comprises re-operating the degree of similarity between the target data and the key data in accordance with the order of the sequence data functioning as the object of extraction by using the involved sequence data as the target data, performing the operation for storing the sum values of the sequence data for the target data occurring at the time of the operation, acquiring the direction selection date created during the operation, and acquiring the optimal disposition for the sequence data of the target data with respect to the sequence data of the key data. With the arrangement of the operations for the dynamic programming by the dynamic programming operation unit, the operations for the dynamic programming can be executed with high efficiency, and the optimal disposition of the sequence data can be acquired efficiently by selecting the target data effectively.

Furthermore, the gene database retrieval system according to this invention is provided with the function for data conversion on the side of the dynamic programming operation unit so that the process can be performed with ease, in correspondence with the appropriate data expression form, even if data of the gene database would be transmitted in various data expression forms.

In addition, as described hereinabove, the gene database retrieval system according to this invention can perform data retrieval for the gene database by allowing the dynamic programming operation unit of the operation unit for exclusive use to determine the degree of similarity between the target data and the key data functioning as the object at a high speed and by selecting the objects of the candidate for extraction by applying the dynamic programming to all the operations. With the arrangement of the exclusive operation unit, the system according to this invention can perform the operations at a high speed without causing any loss in data retrieval, particularly during the selections process, which may have occurred in conventional methods. Further, the gene data-base retrieval system according to this invention can perform the retrieval (homology retrieval) with as high a degree of accuracy and in as short a practical processing time as the computation method with the altered conventional algorithm.

What is claimed is:

1. A gene database retrieval system comprising:

a gene database for storing a sequence data of at least either of sequences of bases of a nucleic acid or sequences of amino acids of a protein, each constituting a gene whose structure has been analyzed and identified;

a dynamic programming operation unit for determining a degree of similarity between a target data and a key data, said target data being constituted by a sequence data of bases from said gene database and said key data being constituted by a sequence data of bases functioning as a retrieval key; and a central processing device unit for parallel-executing an access process of making access to said gene database and an operation process of determining the degree of similarity by entering a sequence data of bases one after another from said gene database as the target data by making controls over both of said gene database and said dynamic programming operation unit;

wherein said central processing device unit for controlling said dynamic programming operation unit comprises:

a first operation control means for executing an operation for determining the degree of similarity between the target data and the key data by altering the target data one after another with respect to the key data, acquiring the sum value of the sequence data of each target data occurring at the operation, and storing only the maximal sum values for the sequence data;

a second operation control means for classifying the maximal sum values of the sequence data of the target data determined by the first operation control means and determining the order of the sequence data as an object of extraction; and a third operation control means for performing a re-operation for determining the degree of similarity between the target data and the key data by utilizing the sequence data for the object of extraction as a target data in accordance with the order of the sequence data functioning as the object of extraction, then performing an operation for storing the sum value of the sequence data of the target data occurring at the time of the operation, acquiring a direction selection data created during the operation, and determining the optimal disposition of the sequence data of the target data with respect to the key data.

2. The gene database retrieval system as claimed in claim 1, wherein said dynamic programming operation unit further comprises a rewritable score memory for storing a score value of the degree of similarity;

wherein said central processing device unit is arranged in order to execute a process for controlling the operation by the third operation control means by altering a portion or a whole of the score values of the degrees of similarity after having stored the score values of the degree of similarity in said score memory and to perform a process for controlling the operation by the first operation control means.

3. The gene database retrieval system as claimed in claim 1, wherein said dynamic programming operation unit further comprises a rewritable score memory for storing the score values of the degree of similarity and holds in said score memory the score values in a non-symmetrical form of a matrix configuration of sequence elements in accordance with sequence elements on the key data side; and wherein said central processing device unit is arranged in order to perform the control of the operation by said first or third operation control means by utilizing the score value of said score memory.

4. The gene database retrieval system as claimed in claim 1, wherein said dynamic programming operation unit comprises a data conversion section for converting a data type into a predetermined form, wherein the sequence data stored in the gene database is compressed or transformed; and wherein said central processing device unit is arranged in order to execute the operation of the dynamic programming by reading the sequence data of the gene database in an intact form, to transmit the read sequence data to the dynamic programming operation unit and to allow the input sequence data to be converted into a predetermined form by the data conversion section of said dynamic programming operation unit.

5. The gene database retrieval system as claimed in claim 1, wherein said dynamic programming operation unit further comprises a data conversion section for converting a data type into a predetermined form, wherein the operation of the dynamic programming is executed by reading the sequence data from the gene database, allowing the read sequence data to be compressed or transformed in the central processing device unit, transmitting the compressed or transformed data to the dynamic programming operation unit, and by allowing the data conversion section of said dynamic programming operation unit to convert the data into a predetermined form.

6. The gene database retrieval system as claimed in claim 1, wherein said third operation control means performs the controls of operations comprising:

an operation for executing the operation for each row until reaching a predetermined length of the key data or the target data;

an operation for acquiring the maximal value of the sum values for each row and for interrupting the operation when the row is found which is identical to the maximal sum value determined by the operation by the first operation control means;

an operation for acquiring the contents of the sum value memory of the involved row and the direction selection data;

an operation for determining the position of the maximal value of the sum values from said sum value memory;

an operation for acquiring the direction selection data corresponding to the position of the maximal value thereof; and an operation for acquiring the direction selection data while re-executing the operation of the dynamic programming on the basis of the direction selection data at least in the position identical to the corresponding position or in one region containing the position or more than the position.

7. The gene database retrieval system as claimed in claim 1, wherein said third operation control means performs the controls of operations comprising:

an operation for executing the operation for each column until reaching a predetermined length of the key data or the target data;

an operation for acquiring the maximal value of the sum values for each column and for interrupting the operation when the column is found which is identical to the maximal sum value determined by the operation by the first operation control means;

an operation for acquiring the contents of the sum value memory of the involved column and the direction selection data;

an operation for determining the position of the maximal value of the sum values from said sum value memory;

an operation for acquiring the direction selection data corresponding to the position of the maximal value thereof; and an operation for acquiring the direction selection data while re-executing the operation of the dynamic programming on the basis of the direction selection data at least in the position identical to the corresponding position or in one region containing the position or more than the position.

8. The gene database retrieval system as claimed in claim 1, further comprising a device for determining a gene sequence, which outputs a sequence data of bases for the retrieval key;

wherein the sequence data of the bases output from said device is input as the key data into said dynamic programming operation unit.

9. The gene database retrieval system as claimed claim 1, wherein the access process for making access to the gene database by said central processing device unit is executed in parallel to the operation process by said dynamic programming operation unit at least for a portion of the time period of the operation of the processes, and wherein said central processing device unit is so arranged as to read the oncoming target data from the gene database prior to the operation by said dynamic programming operation unit during the period of time during which the operation is being executed by said dynamic programming operation unit.

10. The gene database retrieval system as claimed in claim 1, wherein said dynamic programming operation unit comprises:

a key memory for storing the key data of the sequence data of bases functioning as the retrieval key;

a target memory for storing the target data of the sequence data from the gene database;

a score memory for storing the definition of the degree of similarity between the individual base elements of the sequence data of the bases;

a basic operation processing section for executing a basic operation of the dynamic programming;

a direction selection memory for storing a record of a direction of selecting a locally optimal value occurring at the time when the basic operation processing section performs the basic operation of the dynamic programming;

a sum value memory for storing the sum values obtained by the operation of the dynamic programming; and a control section for controlling the operation of the dynamic programming by controlling each of said memories and said basic operation processing section.

11. The gene database retrieval system as claimed in claim 10, wherein said dynamic programming operation unit further comprises:

a constant register for storing a constant value for use in comparing the sum values acquired by the operation of said dynamic programming; and an operation element for replacing the sum value with the constant value when the sum value is brought into a given relationship with the constant value of the constant register.

12. The gene database retrieval system as claimed in claim 10, wherein said dynamic programming operation unit further comprises:

a constant register for storing a constant value in comparing the sum value acquired by the operation of said dynamic programming; and an operation element for generating a signal to suspend the operation element when the sum value resulting from the operation is brought into a given relationship with the constant value of the constant register.

* * * * *